United States Patent
Seitz et al.

(10) Patent No.: US 6,313,173 B1
(45) Date of Patent: Nov. 6, 2001

(54) GLYOXYLIC ACID AMIDES

(75) Inventors: Thomas Seitz, Langenfeld; Klaus Stenzel, Düsseldorf, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/308,074

(22) PCT Filed: Nov. 7, 1997

(86) PCT No.: PCT/EP97/06187

§ 371 Date: May 12, 1999

§ 102(e) Date: May 12, 1999

(87) PCT Pub. No.: WO98/22434

PCT Pub. Date: May 28, 1998

(30) Foreign Application Priority Data

Nov. 20, 1996 (DE) .............................................. 196 48 009

(51) Int. Cl.⁷ .......................... A01N 37/50; C07C 251/48; C07C 251/86
(52) U.S. Cl. ............................ 514/599; 514/620; 564/74; 564/164
(58) Field of Search ..................... 564/74, 164; 514/599, 514/620

(56) References Cited

U.S. PATENT DOCUMENTS

| | | | |
|---|---|---|---|
| 5,057,146 | 10/1991 | Anthony et al. | 71/94 |
| 5,112,860 | 5/1992 | Wingert et al. | 514/513 |
| 5,145,856 | 9/1992 | Clough et al. | 514/274 |
| 5,187,170 | 2/1993 | Wingert et al. | 514/351 |
| 5,221,762 | 6/1993 | Wingert et al. | 560/35 |
| 5,264,440 | 11/1993 | Clough et al. | 514/269 |
| 5,286,894 | 2/1994 | Bushell et al. | 560/55 |
| 5,315,025 | 5/1994 | Bushnell et al. | 560/60 |
| 5,395,837 | 3/1995 | Clough et al. | 514/269 |
| 5,521,146 | * 5/1996 | Hur et al. | 504/243 |
| 5,633,256 | 5/1997 | Anthony et al. | 514/256 |
| 5,709,867 | * 1/1998 | Bernardon | 424/401 |
| 5,849,751 | * 12/1998 | Muller et al. | 514/292 |
| 5,990,171 | * 11/1999 | Seitz et al. | 514/614 |
| 6,130,251 | 10/2000 | Seitz et al. | 514/620 |

FOREIGN PATENT DOCUMENTS

| | | |
|---|---|---|
| 3938054 | 5/1991 | (DE) . |
| 4443641 | 6/1996 | (DE) . |
| 19512617 | 10/1996 | (DE) . |
| 19629463 | 1/1998 | (DE) . |
| 19629464 | 1/1998 | (DE) . |
| 19629465 | 1/1998 | (DE) . |
| 51-91284 | * 10/1976 | (JP) . |
| WO 96/23763 | * 8/1996 | (WO) . |

OTHER PUBLICATIONS

Seitz et al., Chemical Abstracts, vol. 123, abstract 340101, 1995.*
J. Heterocycle Chem., Mar.–Apr. 1990, 27(3), pp. 487–495.
Farmco Ed. Sci. (month unavailable) 1980, 35(5), pp. 394–404.
Justus Liebigs Ann. Chem. (month unavailable) 1969 pp. 29–37.
Justus Liebigs Ann. Chem. (month unavailable) 1969, 722, pp. 38–44.
Tetrahedron, (month unavailable) 1971, pp. 3431–3436.

* cited by examiner

*Primary Examiner*—Richard L. Raymond
(74) *Attorney, Agent, or Firm*—Norris McLaughlin & Marcus

(57) ABSTRACT

The invention relates to novel glyoxylic acid amides, to a process for their preparation and to their use as pesticides.

9 Claims, No Drawings

GLYOXYLIC ACID AMIDES

TECHNICAL FIELD OF THE INVENTION

The invention relates to novel glyoxylic acid amides, to a plurality of processes for their preparation and to their use as pesticides.

DETAILED DESCRIPTION OF THE INVENTION

Novel compounds of the general formula (I) have been found

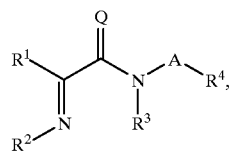
(I)

in which
- A represents optionally substituted branched alkanediyl, represents optionally substituted straight-chain or branched alkanediyl which is interrupted by one or more hetero atoms, represents optionally substituted cycloalkanediyl or represents optionally substituted phenylene,
- Q represents oxygen or sulphur,
- $R^1$ represents in each case optionally substituted cycloalkyl, cycloalkenyl, aryl or heterocyclyl,
- $R^1$ represents aryl having a fused-on cycloalkyl ring where both the aryl moiety and the cycloalkyl moiety optionally carry further substituents, or
- $R^1$ represents optionally substituted benzoheterocyclyl having one, two or three hetero atoms, or
- $R^1$ represents a tricycle

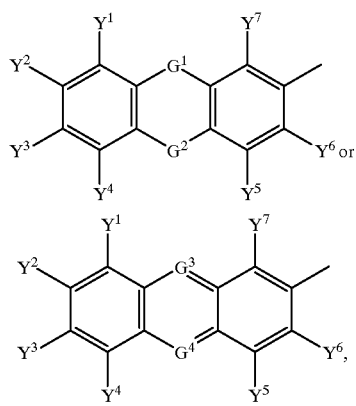

in which
- $G^1$ and $G^2$ independently of one another each represent a single bond, alkanediyl, alkenediyl, oxygen, sulphur, —NH—, —N(alkyl)- or carbonyl,
- $G^3$ and $G^4$ independently of one another each represent nitrogen or a grouping

and
- $Y^1, Y^2, Y^3, Y^4, Y^5, Y^6, Y7$ and Y8 independently of one another each represent hydrogen, halogen, cyano, nitro, in each case optionally substituted alkyl, alkoxy, alkylamino, dialkylamino, alkylthio, alkylsulphinyl, alkylsulphonyl or cycloalkyl,
- $R^2$ represents hydroxyl, amino or in each case optionally substituted alkyl, alkenyl, alkinyl, alkoxy, alkenyloxy, alkinyloxy, alkylamino, dialkylamino, arylamino, cycloalkyl, cycloalkenyl, cycloalkoxy, cycloalkenyloxy, cycloalkylamino, aryl, arylalkyl, arylalkoxy or heterocyclyl or one of the following groupings:

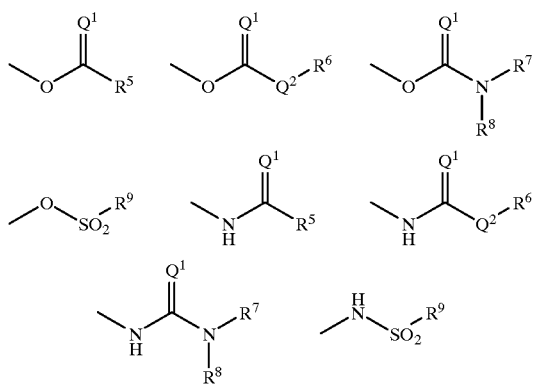

in which
- $Q^1$ and $Q^2$ independently of one another each represent oxygen or sulphur,
- $R^5$ represents hydrogen or optionally substituted alkyl or aryl,
- $R^6$ represents optionally substituted alkyl or aryl,
- $R^7$ represents hydrogen or optionally substituted alkyl or aryl,
- $R^8$ represents optionally substituted alkyl or aryl, or
- $R^7$ and $R^8$ together with the linking nitrogen atom represent an optionally alkyl-substituted heterocyclic ring,
- $R^9$ represents optionally substituted alkyl, dialkylamino, saturated heterocyclyl which is attached via nitrogen, or represents aryl,
- $R^3$ represents hydrogen or in each case optionally substituted alkyl, alkenyl, alkinyl or cycloalkyl,
- $R^4$ represents in each case optionally substituted cycloalkyl, cycloalkenyl, aryl or heterocyclyl.

In the definitions, the saturated or unsaturated hydrocarbon chains, such as alkyl, alkanediyl, alkenyl or alkinyl, are in each case straight-chain or branched, including in combination with hetero atoms, such as in alkoxy, alkylthio or alkylamino. If an alkyl or alkanediyl chain is interrupted by more than one hetero atom, these are identical or different. If a hetero atom represents nitrogen, it is optionally substituted by alkyl, preferably alkyl having 1 to 4 carbon atoms. If an alkyl or alkanediyl chain is interrupted by more than one oxygen atom, these oxygen atoms are not directly adjacent. Hetero atoms may be positioned both at the beginning, in the middle or at the end of the chain.

Halogen generally represents fluorine, chlorine, bromine or iodine, preferably fluorine, chlorine or bromine, in particular fluorine or chlorine.

Aryl represents aromatic, mono- or polycyclic hydrocarbon rings, such as, for example, phenyl, naphthyl, anthranyl, phenanthryl, preferably phenyl or naphthyl, in particular phenyl.

Heterocyclyl represents saturated or unsaturated, and also aromatic, cyclic compounds in which at least one ring member is a hetero atom, i.e. an atom which is different from carbon. If the ring contains a plurality of hetero atoms, these may be identical or different. Preferred hetero atoms are oxygen, nitrogen or sulphur. If the ring contains a plurality of oxygen atoms, these oxygen atoms are not directly adjacent.

If appropriate, cyclic compounds form, together with other carbocyclic or heterocyclic fused-on or bridged rings, a polycyclic ring system. Preference is given to mono- or bicyclic ring systems, in particular to mono- or bicyclic aromatic ring systems.

Cycloalkyl represents saturated carbocyclic cyclic compounds which may, if appropriate, form a polycyclic ring system together with other carbocyclic fused-on or bridged rings.

Cycloalkenyl represents carbocyclic cyclic compounds which contain at least one double bond and which may, if appropriate, form a polycyclic ring system together with other carbocyclic fused-on or bridged rings.

Benzoheterocyclyl represents a heterocyclic ring having a fused-on benzene ring.

Finally, it has been found that the novel glyoxylic acid amides of the general formula (I) have very strong fungicidal activity.

If appropriate, the compounds according to the invention are present as mixtures of various possible isomeric forms, in particular of stereoisomers, such as, for example, E and Z, cis or trans, threo and erythro, and also optical isomers. Both the E and the Z isomers, and also the threo and erythro, and also the optical isomers, and any mixtures of these isomers are described and claimed.

The invention preferably provides compounds of the formula (I) in which

A represents branched alkanediyl having 3 to 6 carbon atoms and being optionally mono- to trisubstituted by identical or different substituents, represents straight-chain or branched alkanediyl having 2 to 6 chain members and being mono- to trisubstituted by identical or different substituents and interrupted by one or two hetero atoms, where the possible substituents are in each case preferably selected from the list below:
halogen, cyano, nitro, amino, hydroxyl, formyl, carboxyl, carbamoyl, thiocarbamoyl;
in each case straight-chain or branched alkoxy, alkylthio, alkylsulphinyl or alkylsulphonyl having in each case 1 to 6 carbon atoms;
in each case straight-chain or branched alkenyl or alkenyloxy having in each case 2 to 6 carbon atoms;
in each case straight-chain or branched halogenoalkoxy, halogenoalkylthio, halogenoalkylsulphinyl or halogenoalkylsulphonyl having in each case 1 to 6 carbon atoms and 1 to 13 identical or different halogen atoms;
in each case straight-chain or branched halogenoalkenyl or halogenoalkenyloxy having in each case 2 to 6 carbon atoms and 1 to 13 identical or different halogen atoms;
in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties;
cycloalkyl having 3 to 6 carbon atoms;
and aryl or heterocyclyl, each of which is optionally mono- or polysubstituted by identical or different substituents selected from the group consisting of
halogen, cyano and straight-chain or branched alkyl having 1 to 4 carbon atoms
and straight-chain or branched halogenoalkyl having 1 to 4 carbon atoms and 1 to 9 identical or different halogen atoms
and straight-chain or branched alkoxy or alkylthio having 1 to 4 carbon atoms
and straight-chain or branched halogenoalkoxy or halogenoalkylthio having 1 to 4 carbon atoms and 1 to 9 identical or different halogen atoms
and in each case doubly attached alkylene or dioxyalkylene having in each case 1 to 6 carbon atoms and being optionally mono- or polysubstituted by identical or different substituents selected from the group consisting of halogen and straight-chain or branched alkyl having 1 to 4 carbon atoms
and straight-chain or branched halogenoalkyl having 1 to 4 carbon atoms and 1 to 9 identical or different halogen atoms, or A represents cycloalkane-1,2-diyl having 3 to 8 carbon atoms or o-phenylene, each of which is optionally mono- to trisubstituted by identical or different substituents, possible substituents being the substituents mentioned above for A, and also alkyl having 1 to 6 carbon atoms and halogenoalkyl having 1 to 4 carbon atoms and 1 to 9 halogen atoms, Q represents oxygen or sulphur, $R^1$ represents cycloalkyl, cycloalkenyl, aryl or heterocyclyl, each of which is optionally mono- to pentasubstituted, where the possible substituents are preferably selected from the list below:
halogen, cyano, nitro, amino, hydroxyl, formyl, carboxyl, carbamoyl, thiocarbamoyl;
in each case straight-chain or branched alkyl, alkoxy, alkylthio, alkylsulphinyl or alkylsulphonyl having in each case 1 to 8 carbon atoms;
in each case straight-chain or branched alkenyl or alkenyloxy having in each case 2 to 6 carbon atoms;
in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
in each case straight-chain or branched halogenoalkenyl or halogenoalkenyloxy having in each case 2 to 6 carbon atoms and 1 to 13 identical or different halogen atoms;
in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties;
cycloalkyl having 3 to 6 carbon atoms;
and aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, each of which is optionally mono- or polysubstituted by identical or different substituents selected from the group consisting of halogen, cyano and straight-chain or branched alkyl having 1 to 4 carbon atoms
and straight-chain or branched halogenoalkyl having 1 to 4 carbon atoms and 1 to 9 identical or different halogen atoms
and straight-chain or branched alkoxy or alkylthio having 1 to 4 carbon atoms
and straight-chain or branched halogenoalkoxy or halogenoalkylthio having 1 to 4 carbon atoms and 1 to 9 identical or different halogen atoms
and in each case doubly attached alkylene or dioxyalkylene having in each case 1 to 6 carbon atoms and being optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms, or $R^1$ represents phenyl or naphthyl having a fused-on cycloalkyl ring having 3 to 10 ring members, where the cycloalkyl moiety is optionally substituted by 1 to 4 alkyl chains having in each case 1–4 carbon atoms and where the phenyl or naphthyl moiety optionally carries the substituents mentioned for $Y^1$ to $Y^8$, or $R^1$ represents benzoheterocyclyl having 3 to 12 ring members in the heterocyclyl moiety and one, two or three hetero atoms and being optionally mono- or polysubstituted by identical or different substituents, where preference is given to the substituents mentioned for $Y^1$ to $Y^8$, or $R^1$ represents a tricycle

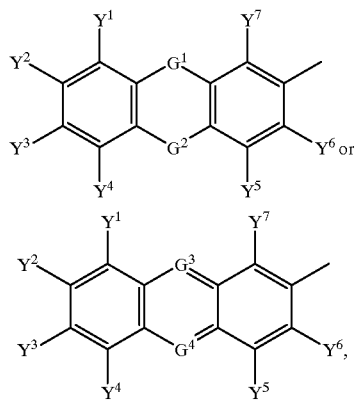

in which
$G^1$ and $G^2$ independently of one another each represent a single bond, alkanediyl having 1 to 3 carbon atoms, alkenediyl having 2 to 3 carbon atoms, oxygen, sulphur, —NH—, —NC$_1$—C$_4$-(alkyl)- or carbonyl,
$G^3$ and $G^4$ independently of one another each represent nitrogen or a grouping

and
$Y^1, Y^2, Y^3, Y^4, Y^5, Y^6, Y^7$ and $Y^8$ independently of one another each represent hydrogen, halogen, cyano, nitro;

alkyl, alkoxy, alkylamino, dialkylamino, alkylthio, alkylsulphinyl or alkylsulphonyl having in each case 1 to 8 carbon atoms in the individual alkyl moieties;
halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms or
cycloalkyl having 3 to 6 carbon atoms, $R^2$ represents hydroxyl, amino or in each case optionally halogen-, cyano- or $C_1$–$C_4$-alkoxy-substituted alkyl, alkenyl, alkinyl, alkoxy, alkenyloxy, alkinyloxy, alkylamino, dialkylamino having in each case 1 to 4 carbon atoms in the individual alkyl moieties, in each case optionally halogen-, cyano-, $C_1$–$C_4$-alkyl- or $C_1$–$C_4$-alkoxy-substituted cycloalkyl, cycloalkenyl, cycloalkoxy, cycloalkenyloxy, cycloalkylamino, having 3 to 8 carbon atoms in the rings in question or in each case optionally substituted phenyl, benzyl, benzyloxy, naphthyl, phenylamino or heterocyclyl having 3 to 8 ring members, where the possible substituents are preferably selected from the list below:
halogen, cyano, nitro, amino, hydroxyl, formyl, carboxyl, carbamoyl, thiocarbamoyl;
in each case straight-chain or branched alkyl, alkoxy, alkylthio, alkylsulphinyl or alkylsulphonyl having in each case 1 to 6 carbon atoms;
in each case straight-chain or branched alkenyl or alkenyloxy having in each case 2 to 6 carbon atoms;
in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
in each case straight-chain or branched halogenoalkenyl or halogenoalkenyloxy having in each case 2 to 6 carbon atoms and 1 to 13 identical or different halogen atoms;
in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties;
in each case doubly attached alkylene or dioxyalkylene having in each case 1 to 6 carbon atoms and being in each case optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms;
cycloalkyl having 3 to 6 carbon atoms or $R^2$ represents one of the groupings below:

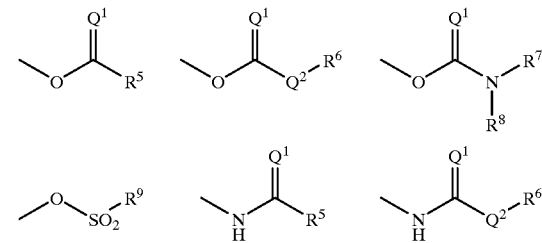

-continued

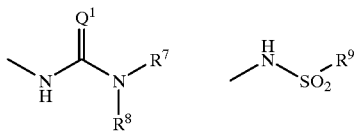

in which
Q$^1$ and Q$^2$ independently of one another each represent oxygen or sulphur,
R$^5$ represents hydrogen or alkyl having 1 to 6 carbon atoms or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms,
R$^6$ represents alkyl having 1 to 6 carbon atoms or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms,
R$^7$ represents hydrogen, alkyl having 1 to 6 carbon atoms or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms,
R$^8$ represents alkyl having 1 to 6 carbon atoms or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms, or
R$^7$ and R$^8$ together with the linking nitrogen atom represent an optionally methyl-substituted heterocyclic ring,
R$^9$ represents alkyl having 1 to 6 carbon atoms, dialkylamino having in each case 1 to 4 carbon atoms in the individual alkyl moieties, heterocyclyl having 3 to 7 ring members which is attached via nitrogen or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms,
R$^3$ represents hydrogen or alkyl having 1 to 4 carbon atoms,
R$^4$ represents aryl, cycloalkyl or cycloalkenyl having 3 to 8 carbon atoms or heterocyclyl having 3 to 12 ring members, each of which is optionally mono- or polysubstituted by identical or different substituents, where the possible substituents are preferably selected from the list below:
halogen, cyano, nitro, amino, hydroxyl, formyl, carboxyl, carbamoyl, thiocarbamoyl;
in each case straight-chain or branched alkyl, alkoxy, alkylthio, alkylsulphinyl or alkylsulphonyl having in each case 1 to 6 carbon atoms;
in each case straight-chain or branched alkenyl or alkenyloxy having in each case 2 to 6 carbon atoms;
in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
in each case straight-chain or branched halogenoalkenyl or halogenoalkenyloxy having in each case 2 to 6 carbon atoms and 1 to 13 identical or different halogen atoms;
in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties;
in each case doubly attached alkylene or dioxyalkylene having in each case 1 to 6 carbon atoms and being in each case optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms;
cycloalkyl having 3 to 6 carbon atoms;
and aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, each of which is optionally mono- or polysubstituted by identical or different substituents selected from the group consisting of
halogen, cyano and straight-chain or branched alkyl having 1 to 4 carbon atoms
and straight-chain or branched halogenoalkyl having 1 to 4 carbon atoms and 1 to 9 identical or different halogen atoms
and straight-chain or branched alkoxy or alkylthio having 1 to 4 carbon atoms
and straight-chain or branched halogenoalkoxy or halogenoalkylthio having 1 to 4 carbon atoms and 1 to 9 identical or different halogen atoms
and in each case doubly attached alkylene or dioxyalkylene having in each case 1 to 6 carbon atoms and being in each case optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms.

The invention in particular relates to compounds of the formula (I) in which
A represents 1,1-, 1,2- or 2,2-propanediyl, 1,1-, 1,2-, 1,3-, 2,2-, 2,3-butanediyl or 1,1-, 1,2- or 1,3-(2-methylpropanediyl), each of which is optionally mono- to trisubstituted by identical or different substituents selected from the group consisting of fluorine, chlorine, cyano and methoxy, or
represents a grouping —O—*CH$_2$—, —NH—*CH$_2$—, —N(CH$_3$)—*CH$_2$—, where the atom labelled with * is attached to R$^4$, or
represents cyclopropane-1,2-diyl, cyclobutane-1,2-diyl, cyclopentane-1,2-diyl, cyclohexane-1,2-diyl, cycloheptane-1,2-diyl or o-phenylene, each of which is optionally mono- to trisubstituted by identical or different substituents selected from the group consisting of methyl, ethyl, fluorine, chlorine, cyano and methoxy,
Q represents oxygen or sulphur,
R$^1$ represents in each case optionally mono- to trisubstituted cyclopropyl, cyclobutyl, cyclopentyl or cyclohexyl, phenyl, naphthyl, furyl, pyrrolyl, thienyl, oxazolyl, isoxazolyl, thiazolyl, isothiazolyl, oxadiazolyl, thiadiazolyl, pyridyl, pyrimidyl, pyridazinyl, pyrazinyl, oxiranyl, oxetanyl, tetrahydrofuryl, perhydropyranyl, pyrrolidinyl, piperidinyl or morpholinyl, where the possible substituents are preferably selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methyl-sulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, cyclopropyl, cyclobutyl, cyclopentyl or cyclohexyl, or $R^1$ represents phenyl or naphthyl having a fused-on cyclopropyl, cyclobutyl, cyclopentyl, cyclohexyl, cycloheptyl cyclooctyl or cyclononyl ring, where the cycloalkyl moiety is optionally mono- to tetrasubstituted by methyl, ethyl, n- or i-propyl, n-, i-, s- or t-butyl and where the phenyl or naphthyl ring optionally carries the substituents mentioned for $Y^1$ to $Y^8$, or $R^1$ represents one of the groupings below

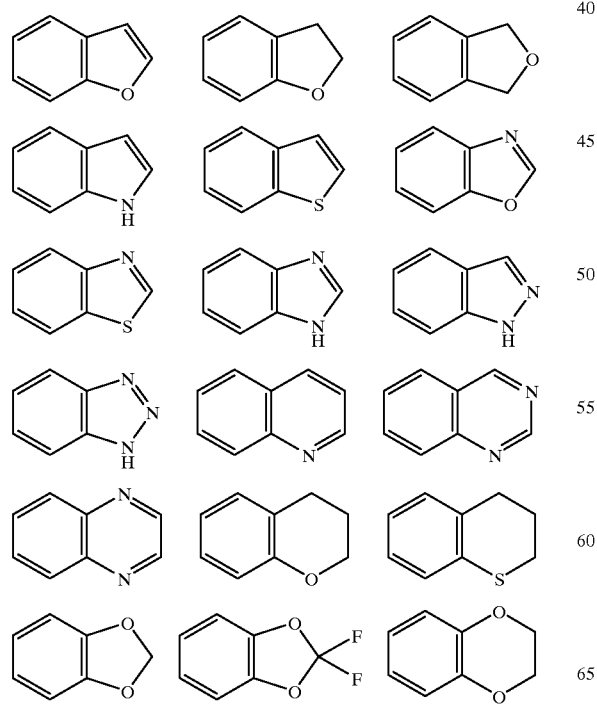

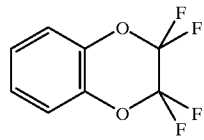

which are in each case attached via any carbon atom and which are furthermore in each case optionally mono- to trisubstituted by identical or different substituents selected from the substituents mentioned for $Y^1$ to $Y^8$, or $R^1$ represents a tricycle

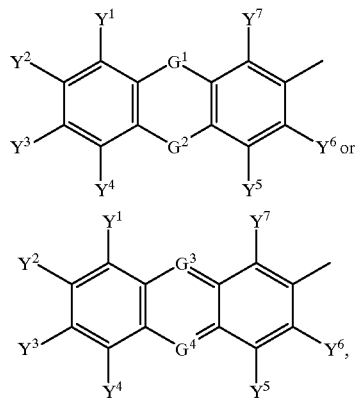

in which $G^2$ and $G^2$ independently of one another in each case represent a single bond, methanediyl, ethanediyl, propanediyl, ethenediyl, oxygen, sulphur, —NH—, —N(CH$_3$)- or carbonyl and $G^3$ and $G^4$ independently of one another each represent nitrogen or a grouping

and $Y^1, Y^2, Y^3, Y^4, Y^5, Y^6, Y^7$ and $Y^8$ independently of one another each represent hydrogen, fluorine, chlorine, bromine, cyano, nitro, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, cyclopropyl, cyclobutyl, cyclopentyl or cyclohexyl, $R^2$ represents hydroxyl, amino or in each case optionally fluorine-, chlorine-, cyano-, methoxy- or ethoxy-substituted methyl, ethyl, n- or i-propyl, n-, i-, s- or t-butyl, vinyl, allyl, propargyl, methoxy, ethoxy, allyloxy, propargyloxy, methylamino, ethylamino, dimethylamino, in each case optionally fluorine-, chlorine-, cyano-, methyl-, ethyl-, methoxy- or ethoxy-substituted cyclopropyl, cyclobutyl, cyclopentyl, cyclohexyl, cyclopentyloxy, cyclohexyloxy, cyclopentylamino, cyclohexylamino or in each case optionally substituted phenyl, benzyl, benzyloxy, naphthyl, phenylamino or heterocyclyl having 3 to 8 ring members, where the possible substituents are preferably selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, in each case doubly attached trimethylene (propane-1,3-diyl), tetramethylene (butane-1,4-diyl), methylenedioxy or ethylenedioxy, each of which is optionally mono- or polysubstituted by identical or different substituents selected from the group consisting of fluorine, chlorine, methyl, trifluoromethyl, ethyl, n- or i-propyl, cyclopropyl, cyclobutyl, cyclopentyl or cyclohexyl, or $R^2$ represents one of the groupings below:

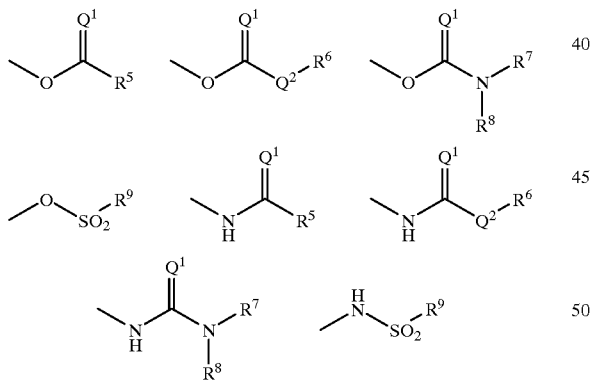

in which $Q^1$ and $Q^2$ independently of one another each represent oxygen or sulphur, $R^5$ represents hydrogen or methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^6$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^7$ represents hydrogen, methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^8$ represents methyl, ethyl, n- or i-propyl, h-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^7$ and $R^8$ together with the linking nitrogen atom represent morpholin-N-yl, piperidin-N-yl, piperazin-N-yl or pyrrolidin-N-yl which is optionally mono- or disubstituted by methyl, $R^9$ represents methyl, ethyl, n- or i-propyl, n-, i-, s- or t-butyl, dimethylamino, diethylamino, pyrrolidin-1-yl, morpholin-N-yl, piperidin-1-yl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^3$ represents hydrogen or represents methyl or ethyl, $R^4$ represents in each case optionally mono- to trisubstituted cyclopropyl, cyclobutyl, cyclopentyl or cyclohexyl, phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl where the possible substituents are preferably selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylarnino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, in each case doubly attached trimethylene (propane-1,3-diyl), tetramethylene (butane-1,4-diyl), methylenedioxy or ethylenedioxy, each of which is optionally mono- or polysubstituted by identical or different substituents selected from the group consisting of fluorine, chlorine, methyl, trifluoromethyl, ethyl, n- and i-propyl, cyclopropyl, cyclobutyl, cyclopentyl or cyclohexyl.

Particular preference is given to compounds of the formula (I) in which

A represents 1,1-, 1,2- or 2,2-propanediyl, 1,1-, 1,2-, 1,3-, 2,2-, 2,3-butanediyl or 1,1-, 1,2- or 1,3-(2-methyl-propanediyl), each of which is optionally mono- to trisubstituted by identical or different substituents selected from the group consisting of fluorine, chlorine, cyano and methoxy, or represents a grouping —O—*CH$_2$—, —NH—*CH$_2$—, —N(CH$_3$)—*CH$_2$—, where the atom labelled with * is attached to R$^4$, or represents cyclopropane-1,2-diyl, cyclobutane-1,2-diyl, cyclopentane-1,2-diyl, cyclohexane- 1,2-diyl, cycloheptane- 1,2-diyl or o-phenylene, each of which is optionally mono- to trisubstituted by identical or different substituents selected from the group consisting of methyl, ethyl, fluorine, chlorine, cyano and methoxy, Q represents oxygen or sulphur, R$^1$ represents in each case optionally mono- to trisubstituted cyclobutyl, cyclopentyl, cyclohexyl, phenyl, naphthyl, furyl, thienyl, pyridyl, tetrahydrofuryl or perhydropyranyl, where the possible substituents are preferably selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl, ethoximinoethyl, cyclopropyl, cyclobutyl, cyclopentyl or cyclohexyl, or R$^1$ represemts a grouping

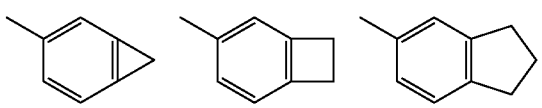

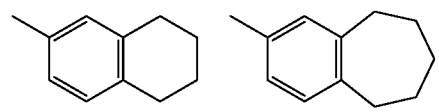

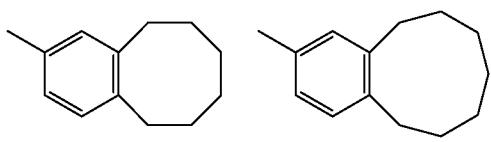

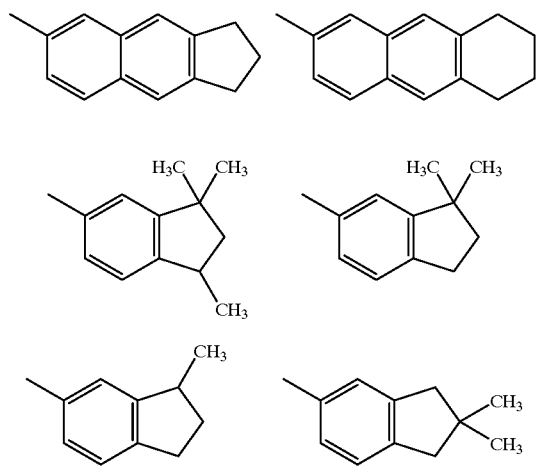

which optionally carries the substituents mentioned for Y$^1$ to Y$^8$ on the phenyl or naphthyl moiety, or R$^1$ represents one of the groupings below

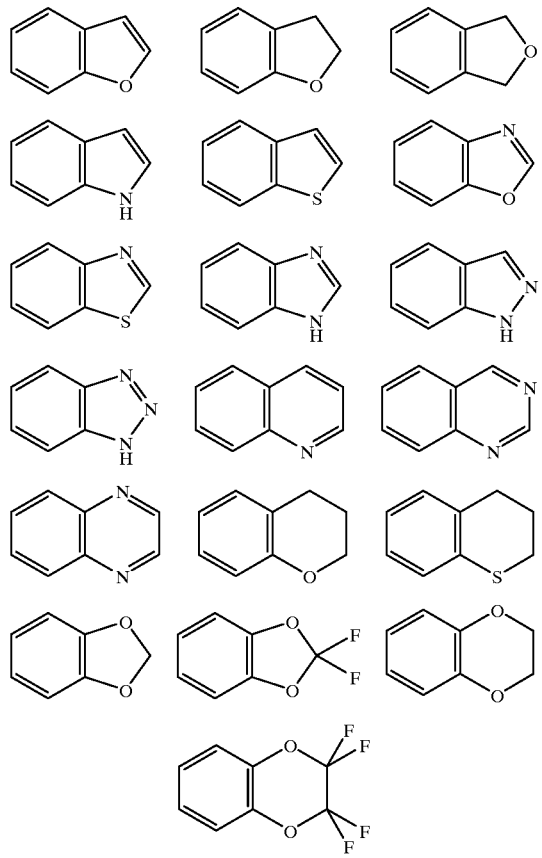

which are in each case attached via any carbon atom and which are furthermore in each case optionally mono- to trisubstituted by identical or different substituents selected from the substituents mentioned for Y$^1$ to Y$^8$, or $R^1$ represents a tricycle
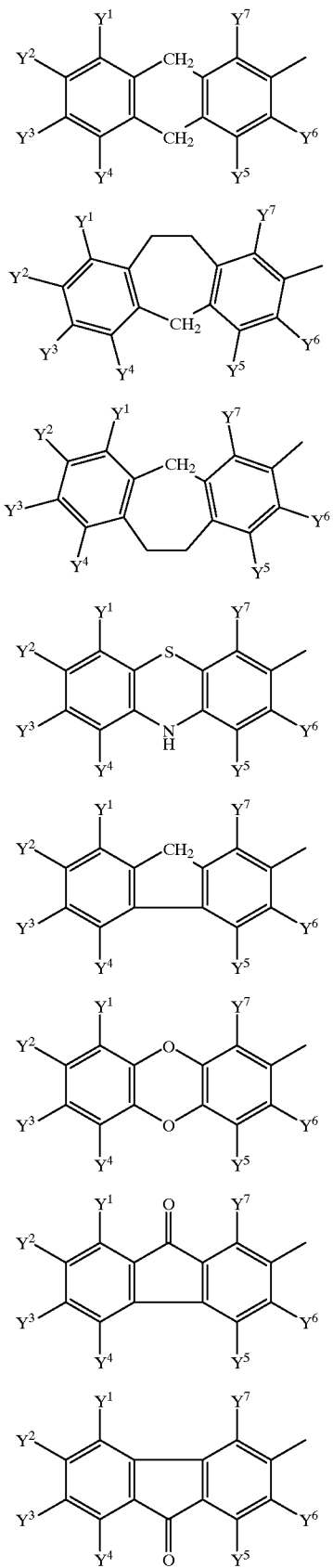
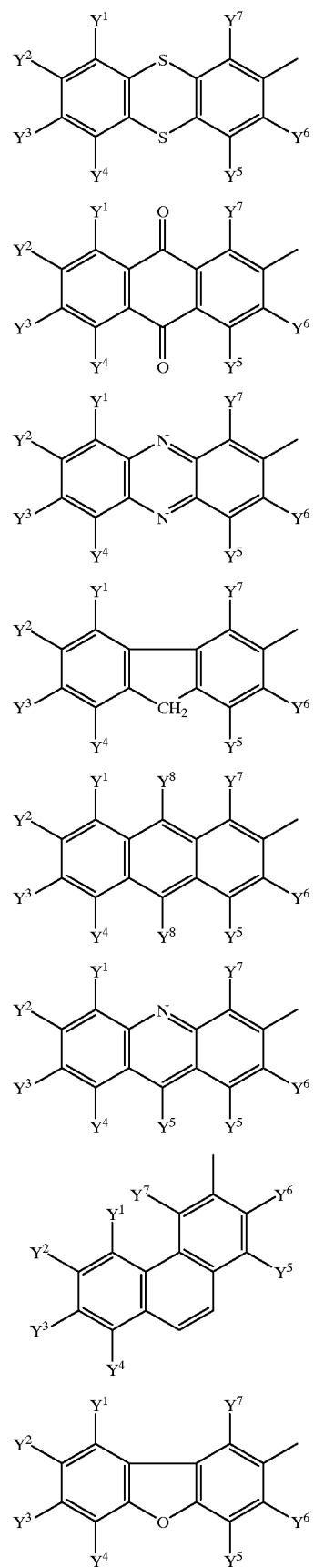

-continued

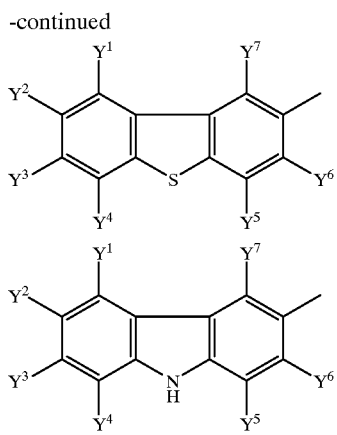

in which

Y¹, Y², Y³, Y⁴, Y⁵, Y⁶, Y⁷ and Y⁸ independently of one another each represent hydrogen, fluorine, chlorine, bromine, cyano, nitro, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, cyclopropyl, cyclobutyl, cyclopentyl or cyclohexyl, R² represents hydroxyl, amino, methyl, fluoromethyl, difluoromethyl, trifluoromethyl, cyanophenyl, ethyl, n- or i-propyl, n-, i-, s- or t-butyl, vinyl, allyl, methoxy, fluoromethoxy, difluoromethoxy, difluorochloromethoxy, trifluoromethoxy, cyanomethoxy, ethoxy, allyloxy, methylamino, ethylamino, dimethylamino, cyclopropyl, cyclobutyl, cyclopentyl, cyclohexyl, cyclopentyloxy, cyclohexyloxy, cyclopentylamino, cyclohexylamino or in each case optionally substituted phenyl, benzyl, benzyloxy, naphthyl, phenylamino, pyrrolidin-1-yl, morpholin-N-yl, piperidin-1-yl, benzofuranyl, thienyl, benzothienyl, pyridyl, quinolyl, tetrahydrofuryl or perhydropyranyl, where the possible substituents are preferably selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, in each case doubly attached trimethylene (propane-1,3-diyl), tetramethylene (butane-1,4-diyl), methylenedioxy or ethylenedioxy, each of which is optionally mono- or polysubstituted by identical or different substituents selected from the group consisting of fluorine, chlorine, methyl, trifluoromethyl, ethyl, n- or i-propyl; cyclopropyl, cyclobutyl, cyclopentyl or cyclohexyl, or R² represents one of the groupings below:

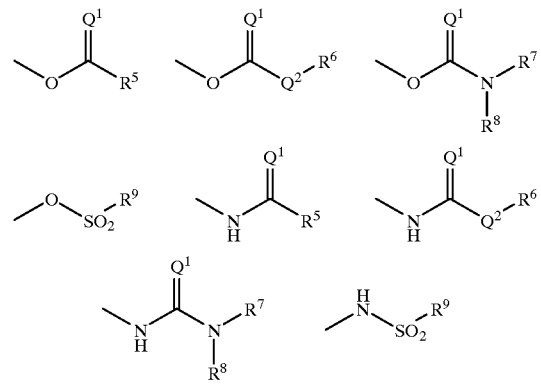

in which

Q¹ and Q² independently of one another each represent oxygen or sulphur,

R⁵ represents hydrogen or methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, R⁶ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, R⁷ represents hydrogen, methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, R⁸ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, or R⁷ and R⁸ together with the linking nitrogen atom represent pyrrolidin-N-yl, morpholin-N-yl, piperidin-N-yl, N'-methyl-piperazin-N-yl, R⁹ represents methyl, ethyl, n- or i-propyl, n-, i-, s- or t-butyl, dimethylamino, diethylamino, pyrrolidin-1-yl, morpholin-N-yl, piperidin-1-yl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, R³ represents hydrogen or represents methyl, R[4] represents in each case optionally mono- to trisubstituted cyclopropyl, cyclobutyl, cyclopentyl, cyclohexyl, phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, where the possible substituents are preferably selected from the list below:

fluorine, chlorine, bromine, cyano, nitro, amino, hydroxyl, formnyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, metboxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, in each case doubly attached trimethylene (propane-1,3-diyl), tetramethylene (butane-1,4-diyl), methylenedioxy or ethylenedioxy, each of which is optionally mono- or polysubstituted by identical or different substituents selected from the group consisting of fluorine, chlorine, methyl, trifluoromethyl, ethyl, n- or i-propyl; cyclopropyl, cyclobutyl, cyclopentyl or cyclohexyl.

A very particularly preferred group of compounds according to the invention are those compounds of the formula (I) in which A represents a grouping

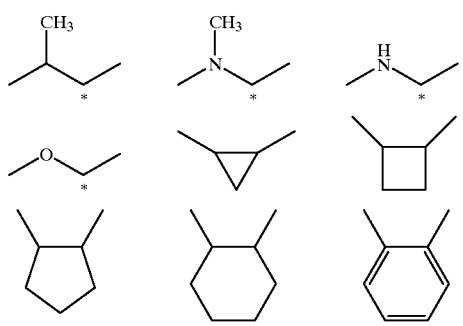

where in each case the atom labelled with * is attached to R[4],

Q represents oxygen,

R[1] represents optionally mono- to trisubstituted phenyl, naphthyl, thienyl or furyl, where the possible substituents are preferably selected from the list below:
bromine, chlorine, fluorine, nitro, methylsulphonyl, phenyl, phenoxy, benzyloxy, cyclopropyl, cyclohexyl, methyl, ethyl, n- or i-propyl, n-, i-, s- or t-butyl, n-pentyl, n-hexyl, n-heptyl, methoxy, ethoxy, trifluoromethyl, trifluoromethoxy and/or methylthio, or R[1] represents a grouping

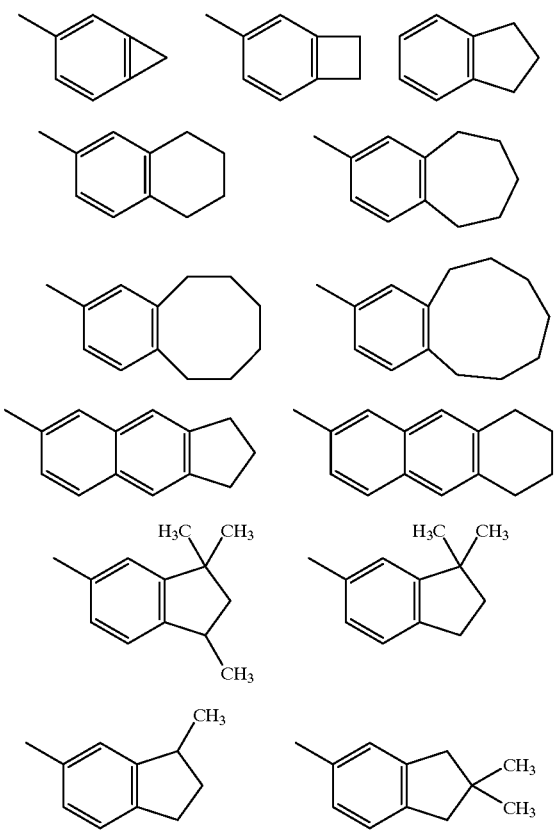

which optionally carries the substituents mentioned for Y[1] to Y[8] on the phenyl or naphthyl moiety, or R[1] represents one of the groupings below

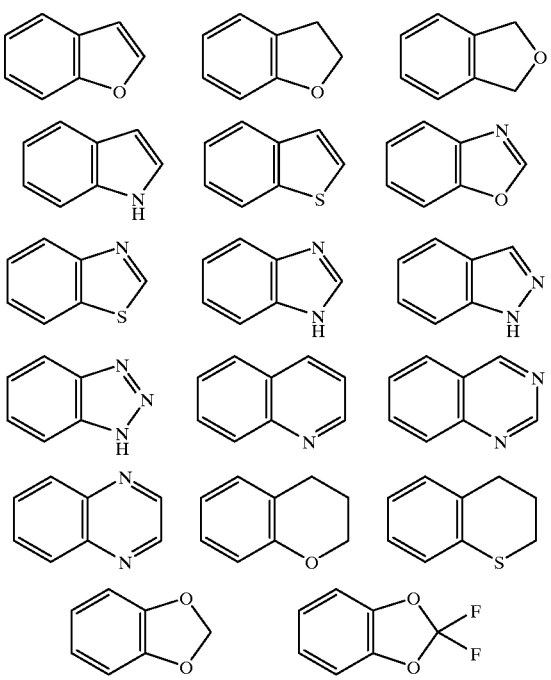

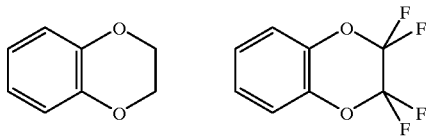
which are in each case attached via any carbon atom and which are in each case optionally mono- to trisubstituted by identical or different substituents selected from the substituents mentioned for $Y^1$ to $Y^8$, or
$R^1$ represents a tricycle
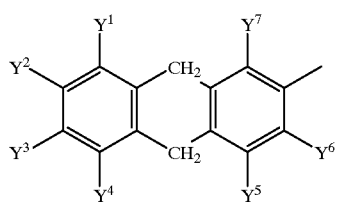
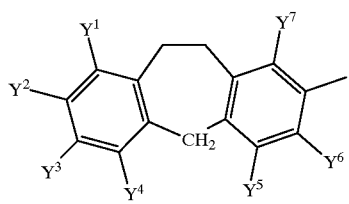
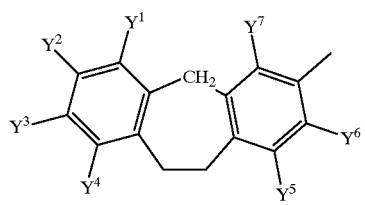
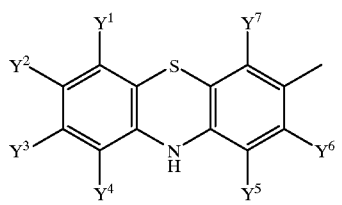
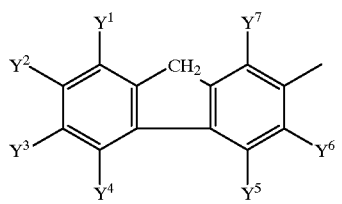
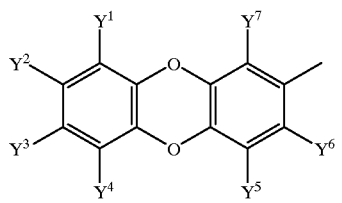
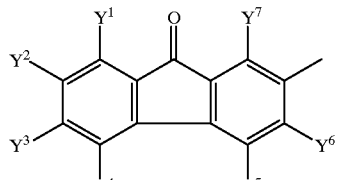
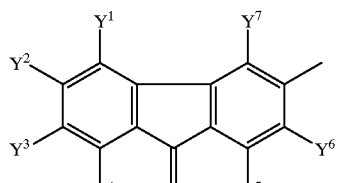
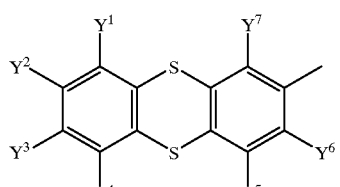
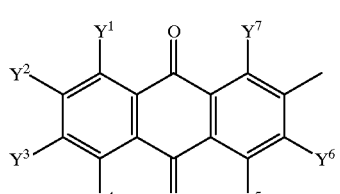
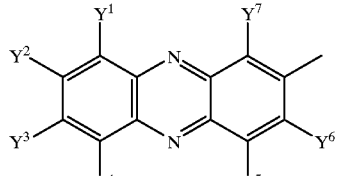
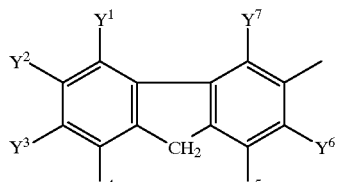
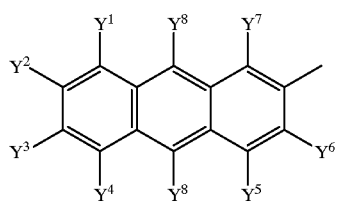
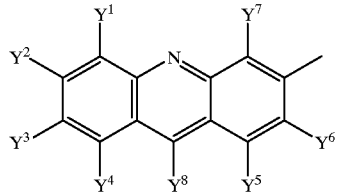

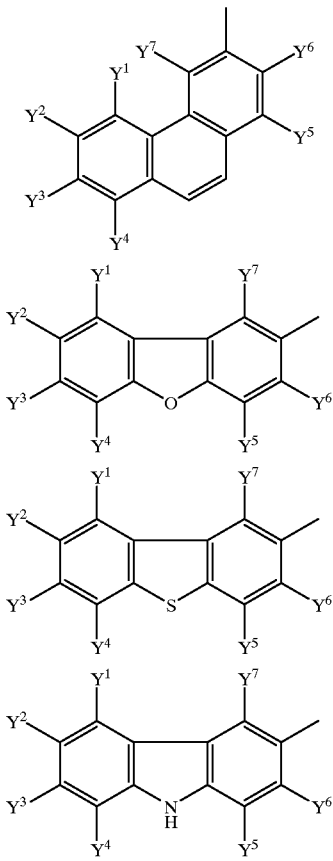

in which

Y¹, Y², Y³, Y⁴, Y⁵, Y⁶, Y⁷ and Y⁸ independently of one another each represent hydrogen, fluorine, chlorine, bromine, cyano, nitro, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, cyclopropyl, cyclobutyl, cyclopentyl or cyclohexyl, $R^2$ represents hydroxyl, amino, methyl, fluoromethyl, difluoromethyl, trifluoromethyl, cyanophenyl, ethyl, n- or i-propyl, n-, i-, s- or t-butyl, vinyl, allyl, methoxy, fluoromethoxy, difluoromethoxy, difluorochloromethoxy, trifluoromethoxy, cyanomethoxy, ethoxy, allyloxy, methylamino, ethylamino, dimethylamino, cyclopropyl, cyclobutyl, cyclopentyl, cyclohexyl, cyclopentyloxy, cyclohexyloxy, cyclopentylamino, cyclohexylamino or in each case optionally substituted phenyl, benzyl, benzyloxy, naphthyl, phenylamino, pyrrolidin-1-yl, morpholin-N-yl, piperidin-1-yl, benzofuranyl, thienyl, benzothienyl, pyridyl, quinolyl, tetrahydrofuryl or perhydropyranyl, where the possible substituents are preferably selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, in each case doubly attached trimethylene (propane-1, 3-diyl), tetramethylene (butane-1,4-diyl), methylenedioxy or ethylenedioxy, each of which is optionally mono- or polysubstituted by identical or different substituents selected from the group consisting of fluorine, chlorine, methyl, trifluoromethyl, ethyl, n- or i-propyl, or $R^2$ represents one of the groupings below:

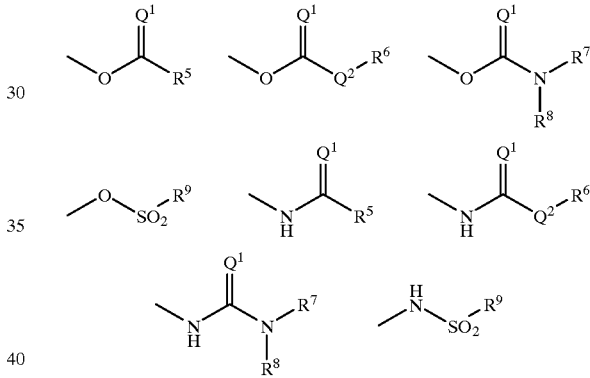

in which $Q^1$ and $Q^2$ each represent oxygen, $R^5$ represents hydrogen or methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^6$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^7$ represents hydrogen, methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^8$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, or $R^7$ and $R^8$ together with the linking nitrogen atom represent pyrrolidin-N-yl, morpholin-N-yl, piperidin-N-yl, N'-methyl-piperazin-N-yl, $R^9$ represents methyl, ethyl, n- or i-propyl, n-, i-, s- or t-butyl, dimethylamino, diethylamino, pyrrolidin-1-yl, morpholin-N-yl, piperidin-1-yl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^3$ represents hydrogen or methyl, $R^4$ represents cyclohexyl or represents optionally mono- to trisubstituted phenyl, thienyl, firyl, benzofuryl, benzothienyl, pyridyl, pyrimidinyl, naphthyl, quinolyl, where the possible substituents are preferably selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, in each case doubly attached trimethylene (propane-1,3-diyl), tetramethylene (butane-1,4-diyl), methyl- enedioxy or ethylenedioxy, each of which is optionally mono- or polysubstituted by identical or different substituents selected from the group consisting of fluorine, chlorine, methyl, trifluoromethyl, ethyl, n- and i-propyl.

Particular preference is also given to compounds of the formula (I) in which $R^2$ represents methoxy, methylamino or dimethylamino.

Particular preference is also given to compounds of the formula (I) in which $R^3$ represents hydrogen.

Particular preference is also given to compounds of the formula (I) in which $R^4$ represents phenyl which is substituted in the 3 and 4 position by methoxy and/or ethoxy.

If A represents cycloalkanediyl, particular preference is given to compounds in which the cycloalkanediyl ring is cis-attached.

The abovementioned general or preferred radical definitions apply both to the end products of the formula (I) and correspondingly to the starting materials or intermediates required in each case for the preparation.

Independently of the combination given in each case, the definitions of radicals given in the combinations or preferred combinations of radicals in question specifically for these radicals can also be replaced by definitions of radicals of other preferred ranges.

Examples of compounds according to the invention are listed in Tables 1 to 6:

TABLE 1

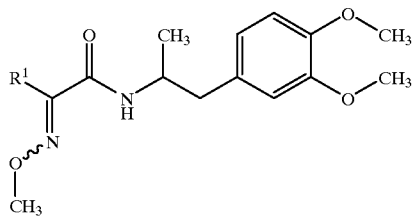

(I-a)

where $R^1$ represents the following substituents:

| Compound No. | $R^1$ | Compound No. | $R^1$ |
|---|---|---|---|
| I-a-1 | | I-a-2 | |
| I-a-3 | | I-a-4 | |
| I-a-5 | | I-a-6 | |

-continued
| Compound No. | R¹ | Compound No. | R¹ |
|---|---|---|---|
| I-a-7 | 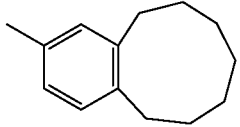 | I-a-8 | 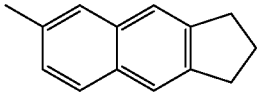 |
| I-a-9 | 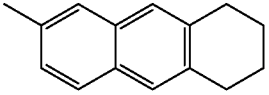 | I-a-10 | 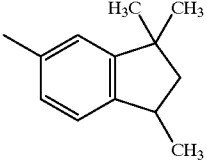 |
| I-a-11 | 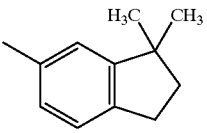 | I-a-12 | 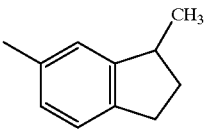 |
| I-a-13 | 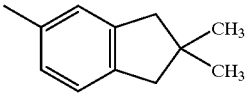 | I-a-14 | 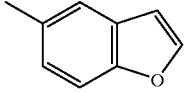 |
| I-a-15 | 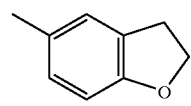 | I-a-16 | 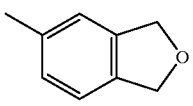 |
| I-a-17 | 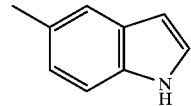 | I-a-18 | 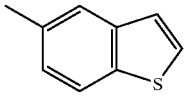 |
| I-a-19 | 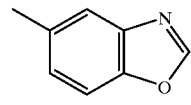 | I-a-20 | 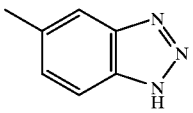 |
| I-a-21 | 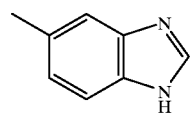 | I-a-22 | 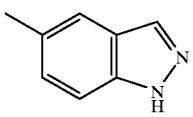 |
| I-a-23 | 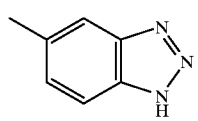 | I-a-24 | 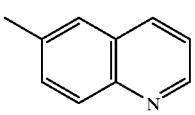 |
| I-a-25 | 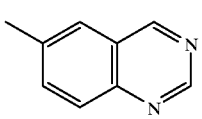 | I-a-26 | 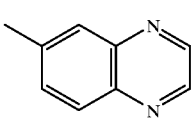 |
| I-a-27 | 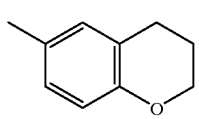 | I-a-28 | 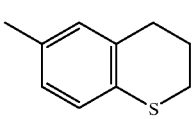 |

-continued
| Compound No. | R¹ | Compound No. | R¹ |
|---|---|---|---|
| I-a-29 | 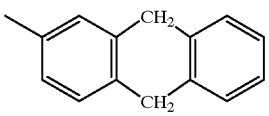 | I-a-30 | 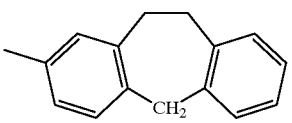 |
| I-a-31 | 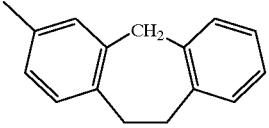 | I-a-32 | 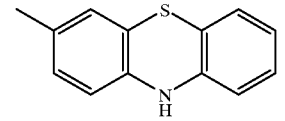 |
| I-a-33 | 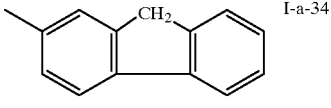 | I-a-34 | 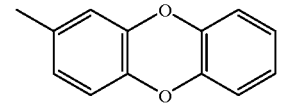 |
| I-a-35 | 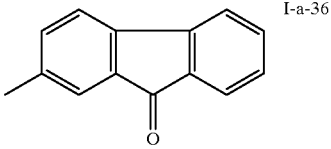 | I-a-36 | 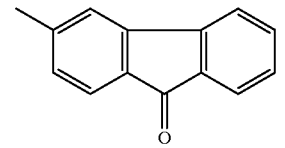 |
| I-a-37 | 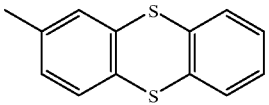 | I-a-38 | 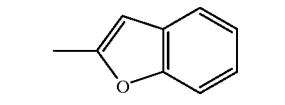 |
| I-a-39 | 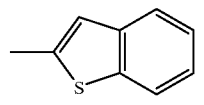 | I-a-40 | 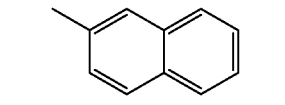 |
| I-a-41 | 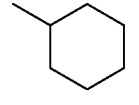 | I-a-42 | 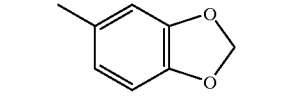 |
| I-a-43 | 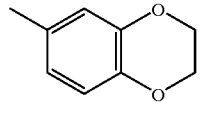 | I-a-44 | 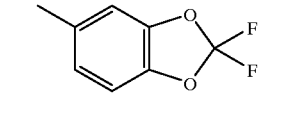 |
| I-a-45 | 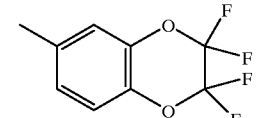 | or | 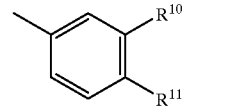 |
| or | 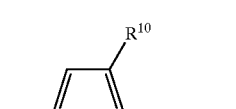 | or | 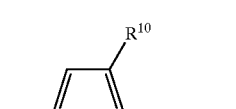 |

-continued

| Compound No. | R¹ | Compound No. | R¹ |
|---|---|---|---|
| or | (4-methyl-furan with R¹⁰ at 3, R¹¹ at 2) | or | (5-methyl-furan with R¹⁰ at 3, R¹¹ at 2) | where R¹⁰ and R¹¹ in case have the following meanings:

| R¹ (phenyl with R¹⁰, R¹¹) | R¹ (4-methylthiophene with R¹⁰, R¹¹) | R¹ (5-methylthiophene with R¹⁰, R¹¹) | R¹ (4-methylfuran with R¹⁰, R¹¹) | R¹ (5-methylfuran with R¹⁰, R¹¹) | | |
|---|---|---|---|---|---|---|
| Compound No. | Compound No. | Compound No. | Compound No. | Compound No | R¹⁰ | R¹¹ |
| I-a-46 | I-8-110 | I-a-174 | I-a-238 | I-a-302 | H | H |
| I-a-47 | I-a-111 | I-a-175 | I-a-239 | I-a-303 | H | chlorine |
| I-a-48 | I-a-112 | I-a-176 | I-a-240 | I-a-304 | H | fluorine |
| I-a-49 | I-a-113 | I-a-177 | I-a-241 | I-a-305 | H | bromine |
| I-a-50 | I-a-114 | I-a-178 | I-a-242 | I-a-306 | H | methyl |
| I-a-51 | I-a-115 | I-a-179 | I-a-243 | I-a-307 | H | ethyl |
| I-a-52 | I-a-116 | I-a-180 | I-a-244 | I-a-308 | H | iso-propyl |
| I-a-53 | I-a-117 | I-a-181 | I-a-245 | I-a-309 | H | n-propyl |
| I-a-54 | I-a-118 | I-a-182 | I-a-246 | I-a-310 | H | n-butyl |
| I-a-55 | I-a-119 | I-a-183 | I-a-247 | I-a-311 | H | iso-butyl |
| I-a-56 | I-a-120 | I-a-184 | I-a-248 | I-a-312 | H | tert-butyl |
| I-a-57 | I-a-121 | I-a-185 | I-a-249 | I-a-313 | H | sec-butyl |
| I-a-58 | I-a-122 | I-a-186 | I-a-250 | I-a-314 | H | methoxy |
| I-a-59 | I-a-123 | I-a-187 | I-a-251 | I-a-315 | H | ethoxy |
| I-a-60 | I-a-124 | I-a-188 | I-a-252 | I-a-316 | H | methylthio |
| I-a-61 | I-a-125 | I-a-189 | I-a-253 | I-a-317 | H | trifluoromethyl |
| I-a-62 | I-a-126 | I-a-190 | I-a-254 | I-a-318 | chlorine | H |
| I-a-63 | I-a-127 | I-a-191 | I-a-255 | I-a-319 | fluorine | H |
| I-a-64 | I-a-128 | I-a-192 | I-a-256 | I-a-320 | bromine | H |
| I-a-65 | I-a-129 | I-a-193 | I-a-257 | I-a-321 | methyl | H |
| I-a-66 | I-a-130 | I-a-194 | I-a-258 | I-a-322 | ethyl | H |
| I-a-67 | I-a-131 | I-a-195 | I-a-259 | I-a-323 | iso-propyl | H |
| I-a-68 | I-a-132 | I-a-196 | I-a-260 | I-a-324 | n-propyl | H |
| I-a-69 | I-a-133 | I-a-197 | I-a-261 | I-a-325 | n-butyl | H |
| I-a-70 | I-a-134 | I-a-198 | I-a-262 | I-a-326 | iso-butyl | H |
| I-a-71 | I-a-135 | I-a-199 | I-a-263 | I-a-327 | tert-butyl | H |
| I-a-72 | I-a-136 | I-a-200 | I-a-264 | I-a-328 | sec-butyl | H |
| I-a-73 | I-a-137 | I-a-201 | I-a-265 | I-a-329 | methoxy | H |
| I-a-74 | I-a-138 | I-a-202 | I-a-266 | I-a-330 | ethoxy | H |
| I-a-75 | I-a-139 | I-a-203 | I-a-267 | I-a-331 | methylthio | H |
| I-a-76 | I-a-140 | I-a-204 | I-a-268 | I-a-332 | trifluoromethyl | H |
| I-a-77 | I-a-141 | I-a-205 | I-a-269 | I-a-333 | chlorine | chlorine |
| I-a-78 | I-a-142 | I-a-206 | I-a-270 | I-a-334 | fluorine | fluorine |
| I-a-79 | I-a-143 | I-a-207 | I-a-271 | I-a-335 | bromine | bromine |
| I-a-80 | I-a-144 | I-a-208 | I-a-272 | I-a-336 | methyl | methyl |
| I-a-81 | I-a-145 | I-a-209 | I-a-273 | I-a-337 | ethyl | ethyl |
| I-a-82 | I-a-146 | I-a-210 | I-a-274 | I-a-338 | methoxy | methoxy |
| I-a-83 | I-a-147 | I-a-211 | I-a-275 | I-a-339 | ethoxy | ethoxy |
| I-a-84 | I-a-148 | I-a-212 | I-a-276 | I-a-340 | methylthio | methylthio |
| I-a-85 | I-a-149 | I-a-213 | I-a-277 | I-a-341 | trifluoromethyl | trifluoromethyl |
| I-a-86 | I-a-150 | I-a-214 | I-a-278 | I-a-342 | chlorine | methyl |
| I-a-87 | I-a-151 | I-a-215 | I-a-279 | I-a-343 | methyl | chlorine |
| I-a-88 | I-a-152 | I-a-216 | I-a-280 | I-a-344 | chlorine | methoxy |
| I-a-89 | I-a-153 | I-a-217 | I-a-281 | I-a-345 | methoxy | chlorine |
| I-a-90 | I-a-154 | I-a-218 | I-a-282 | I-a-346 | chlorine | ethyl |
| I-a-91 | I-a-155 | I-a-219 | I-a-283 | I-a-347 | ethyl | chlorine |
| I-a-92 | I-a-156 | I-a-220 | I-a-284 | I-a-348 | methoxy | ethoxy |

-continued

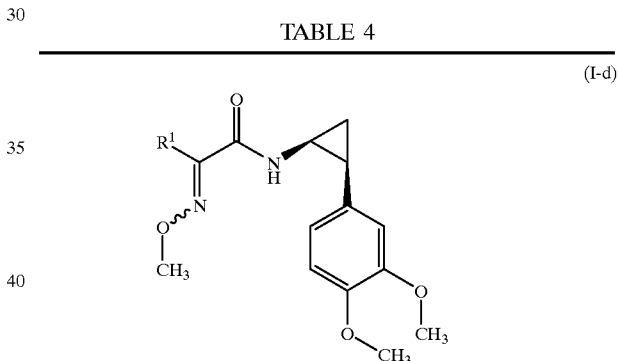

| Compound No. | Compound No. | Compound No. | Compound No. | Compound No | $R^{10}$ | $R^{11}$ |
|---|---|---|---|---|---|---|
| I-a-93 | I-a-157 | I-a-221 | I-a-285 | I-a-349 | ethoxy | methoxy |
| I-a-94 | I-a-158 | I-a-222 | I-a-286 | I-a-350 | methyl | methoxy |
| I-a-95 | I-a-159 | I-a-223 | I-a-287 | I-a-351 | methoxy | methyl |
| I-a-96 | I-a-160 | I-a-224 | I-a-288 | I-a-352 | methyl | ethyl |
| I-a-97 | I-a-161 | I-a-225 | I-a-289 | I-a-353 | ethyl | methyl |
| I-a-98 | I-a-162 | I-a-226 | I-a-290 | I-a-354 | methoxy | ethyl |
| I-a-99 | I-a-163 | I-a-227 | I-a-291 | I-a-355 | ethyl | methoxy |
| I-a-100 | I-a-164 | I-a-228 | I-a-292 | I-a-356 | H | nitro |
| I-a-101 | I-a-165 | I-a-229 | I-a-293 | I-a-357 | H | methylsulphonyl |
| I-a-102 | I-a-166 | I-a-230 | I-a-294 | I-a-358 | H | phenoxy |
| I-a-103 | I-a-167 | I-a-231 | I-a-295 | I-a-359 | H | phenyl |
| I-a-104 | I-a-168 | I-a-232 | I-a-296 | I-a-360 | H | benzyloxy |
| I-a-105 | I-a-169 | I-a-233 | I-a-297 | I-a-361 | H | pentyl |
| I-a-106 | I-a-170 | I-a-234 | I-a-298 | I-a-362 | H | hexyl |
| I-a-107 | I-a-171 | I-a-235 | I-a-299 | I-a-363 | H | heptyl |
| I-a-108 | I-a-172 | I-a-236 | I-a-300 | I-a-364 | H | cyclopropyl |
| I-a-109 | I-a-173 | I-a-237 | I-a-301 | I-a-365 | H | cyclohexyl |

TABLE 2

(I-b)

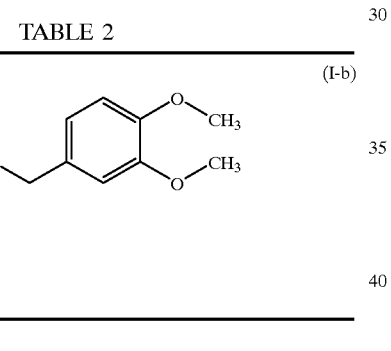

Compounds I-b-1 to I-b-365 where $R^1$ represents the substituents mentioned in Table 1.

TABLE 3

(I-c)

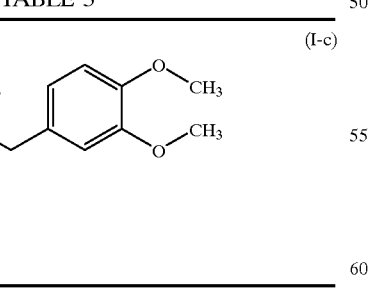

Compounds I-c-1 to I-c-365 where $R^1$ represents the substituents mentioned in Table 1.

TABLE 4

(I-d)

Compounds I-d-1 to I-d-365 where $R^1$ represents the substituents mentioned in Table 1.

Table 5

Compounds I-e-1 to I-e-365, corresponding to the formula I-a, compounds I-f-1 to I-f-365, corresponding to the formula I-b, compounds I-g-1 to I-g-365, corresponding to the formula I-c and compounds I-h-1 to I-h-365, corresponding to the formula I-d, where in each case instead of the 3,4-dimethoxyphenyl group (generally referred to as $R^4$) there is located a 3-ethoxy4-methoxyphenyl group.

Table 6

Compounds I-i-1 to I-i-365, corresponding to the formula I-a, compounds I-j-1 to I-j-365, corresponding to the formula I-b, compounds I-k-1 to I-k-365, corresponding to the formula I-c and compounds I-1-1 to I-1-365, corresponding to the formula I-d, where in each case instead of the 3,4-dimethoxyphenyl group (generally referred to as $R^4$) there is located a 4-ethoxy-3-methoxyphenyl group.

Furthermore, it has been found that the novel glyoxylic acid amides of the general formula (I) are obtained when a) carboxylic acid derivatives of the general formula (II)

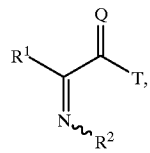
(II)

in which
R¹, R² and Q are each as defined above and
T represents hydroxyl, halogen or alkoxy,
are reacted with an amine of the general formula (III)

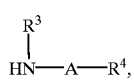
(III)

in which
R³, R⁴ and A are each as defined above
— or with a hydrogen halide thereof—
if appropriate in the presence of an acid acceptor, if appropriate in the presence of a condensing agent and if appropriate in the presence of a diluent, or when b) glyoxylic acid amides of the general formula (IV)

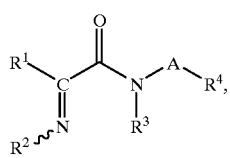
(IV)

in which
A, R¹, R², R³ and R⁴ are each as defined above,
are reacted with a sulphurizing agent, if appropriate in the presence of a diluent, or when c) glyoxylic acid derivatives of the formula (V)

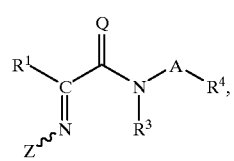
(V)

in which
A, Q, R¹, R³ and R⁴ are each as defined above and
Z represents hydroxyl or amino,
are reacted with an activated acid derivative of one of the formulae (VI) to (XIII),

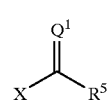
(VI)

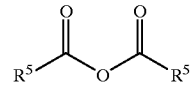
(VII)

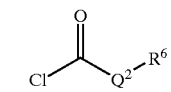
(VIII)

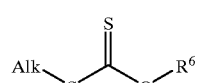
(IX)

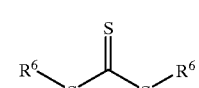
(X)

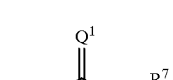
(XI)

$R^7—N=C=O$
(XII)

$R^9—SO_2Cl$
(XIII)

in which
R⁵, R⁶, R⁷, R⁸ and R⁹ are each as defined above,
if appropriate in the presence of a diluent and if appropriate in the presence of a base.

The formula (II) provides a general definition of the carboxylic acid derivatives required as starting materials for carrying out the process a) according to the invention. In this formula (II), Q, R¹ and R² each preferably or in particular have those meanings which have already been mentioned in connection with the description of the compounds of the formula (I) according to the invention as being preferred or as being particularly preferred for Q, R¹ and R²; T preferably represents alkoxy having 1 to 4 carbon atoms, in particular methoxy or ethoxy, or hydroxyl or chlorine.

The starting materials of the formula (II) are known and/or can be prepared by known processes (cf. EP-A 178 826, EP-A 242 081, EP-A 382 375, EP-A 493 711, EP-A 432 503, DE-A 3 938 054, J. Heterocycl. Chem. (1990), 27(3), 487–95, Farmaco, Ed. Sci. (1980), 35(5), 394–404, Justus Liebigs Ann. Chem. (1969), 722, 38–44, Justus Liebigs Ann. Chem. (1969), 722, 29–37, Tetrahedron 1971, 3431–6).

The formula (III) provides a general definition of the amines furthermore required as starting materials for carrying out the process a) according to the invention. In this formula (III), R³, R⁴ and A each preferably or in particular have those meanings which have already been mentioned in connection with the description of the compounds of formula (I) according to the invention as being preferred or as being particularly preferred for R³, R⁴ and A.

The amines of the formula (III) are known organic chemicals for synthesis and/or can be prepared by processes which are known per se.

The formula (IV) provides a general definition of the glyoxylic acid amides required as starting materials for carrying out the process b) according to the invention. In this formula (IV), A, R¹, R², R³ and R⁴ each preferably or in particular have those meanings which have already been mentioned in connection with the description of the compounds of the formula (I) according to the invention as being preferred or as being particularly preferred for A, $R^1$, $R^2$, $R^3$ and $R^4$.

The glyoxylic acid amides of the general formula (IV) are compounds according to the invention and can be obtained by the processes a) or c) according to the invention.

Suitable sulphurizing agents for carrying out the process b) according to the invention are all reagents which are capable of exchanging oxygen atoms which are bound to carbon for sulphur atoms, such as, for example, hydrogen sulphide, phosphorus pentasulphide or Lawesson's reagent.

The formula (V) provides a general definition of the glyoxylic acid derivatives required as starting materials for carrying out the process c) according to the invention. In this formula (V), A, Q, $R^1$, $R^3$ and $R^4$ each preferably in particular have those meanings which have already been mentioned in connection with the description of the compounds of the formula (I) according to the invention as being preferred or as being particularly preferred for A, Q, $R^1$, $R^3$ and $R^4$. Z represents hydroxyl or amino.

The starting materials of the formula (V) are compounds according to the invention and can be obtained by the processes a) or b) according to the invention.

The formulae (VI) to (XIII) provide a general definition of the activated acid derivatives furthermore required for carrying out the process c) according to the invention for preparing the compounds of the formula (I) according to the invention. In these formulae (VI) to (XIII), $R^5$, $R^6$, $R^7$, $R^8$ and $R^9$ each preferably or in particular have those meanings which have already been mentioned in connection with the description of the compounds of the formula (I) according to the invention as being preferred or as being particularly preferred for $R^5$, $R^6$, $R^7$, $R^8$ and $R^9$.

The activated acid derivatives of the formulae (VI) to (XIII) are known organic chemicals for synthesis and/or can be prepared by processes known per se.

The process a) according to the invention is, if appropriate, carried out in the presence of a diluent. Suitable diluents are water and organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethyl-phosphoric triamide; esters such as methyl acetate or ethyl acetate, sulphoxides, such as dimethyl sulphoxide, alcohols, such as methanol, ethanol, n- or i-propanol, ethylene glycol, ethylene glycol monomethyl ether, ethylene glycol monoethyl ether, diethylene glycol monomethyl ether, diethylene glycol monoethyl ether, mixtures thereof with water or pure water.

The process a) according to the invention is, if appropriate, carried out in the presence of a suitable acid acceptor. Suitable acid acceptors are all customary inorganic or organic bases. These include, in particular, alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethyl-benzylamine, pyridine, N-methylpiperidine, N,N-dimethylaminopyridine, diazabicyclooctane (DABCO), diazabicyclononene (DBN) or diazabicycloundecene (DBU).

The process a) according to the invention is, if appropriate, carried out in the presence of a suitable condensing agent. Suitable condensing agents are all condensing agents which are customarily useable for such amidation reactions. Examples which may be mentioned are acyl halide formers such as phosgene, phosphorus tribromide, phosphorus trichloride, phosphorus pentachloride, phosphorus oxychloride or thionyl chloride; anhydride formers such as ethyl chloroformate, methyl chloroformate, isobutyl chloroformate or methanesulphonyl chloride; carbodiimides, such as N,N'-dicyclohexylcarbodiimide (DCC) or other customary condensing agents, such as phosphorus pentoxide, polyphosphoric acid, N,N'-carbonyldiimidazole, 2-ethoxy-N-ethoxycarbonyl-1,2-dihydroquinoline (EEDQ) or triphenylphosphine/carbon tetrachloride.

The process a) according to the invention is, if appropriate, carried out in the presence of a catalyst. Examples which may be mentioned are 4-dimethylaminopyridine, 1-hydroxy-benzotriazole or dimethylformamide.

When carrying out the process a) according to the invention, the reaction temperatures can be varied within a relatively wide range. In general, the reaction is carried out at temperatures between −50° C. and +150° C., preferably at temperatures between −20° C. and 150° C.

For carrying out the process a) according to the invention, generally 1 to 5 mol, preferably 1.0 to 2.5 mol, of amine are employed per mole of carboxylic acid derivative of the formula (II).

The practice of the reaction and the work-up and isolation of the reaction products are carried out by known processes (cf. the Preparation Examples).

The process a) according to the invention can also be carried out as a two-step process. Here, the carboxylic acid derivatives of the general formula (II) are initially converted into an activated form and, in a subsequent step, reacted with the amines of the general formula (III) to give the glyoxylic acid amides of the general formula (I) according to the invention.

Suitable activated forms of the carboxylic acid derivatives of the formula (II) are all carboxy-activated derivatives, such as, for example, acyl halides, preferably acyl chlorides, acid azides, furthermore symmetrical and mixed anhydrides, such as, for example, the mixed o-alkylcarbonic anhydrides, furthermore activated esters, such as, for example, p-nitrophenyl esters or N-hydroxysuccinimide esters, and also adducts with condensing agents, such as, for example, dicyclohexylcarbodiimide, or activated forms of the carboxylic acids which are generated in situ.

Suitable diluents for carrying out the process b) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole.

When carrying out the process b) according to the invention, the reaction temperatures can be varied within a relatively wide range. In general, the reaction is carried out at temperatures from 0° C. to 150° C., preferably at temperatures from 0° C. to 80° C.

For carrying out the process b) according to the invention for preparing the compounds of the formula (I), generally 0.1 to 15 mol, preferably 0.5 to 8 mol, of sulphurizing agent are employed per mole of the glyoxylic acid amide of the formula (IV). Suitable diluents for carrying out the process c) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethyl-formamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide; or sulphones, such as sulpholane.

The process c) according to the invention is, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process c) according to the invention, the reaction temperatures can be varied within a relatively wide range. In general, the reaction is carried out at temperatures from 0° C. to 150° C., preferably at temperatures from 0° C. to 80° C.

For carrying out the process c) according to the invention for preparing the compounds of the formula (I), generally 1 to 15 mol, preferably 2 to 8 mol, of activated acid derivative of one of the formulae (VI) to (XIII) are employed per mole of the glyoxylic acid derivative of the formula (V).

The processes according to the invention are generally carried out under atmospheric pressure. However, it is also possible to operate under elevated or reduced pressure—in general between 0.1 bar and 10 bar.

The practice of the reaction and the work-up and the isolation of the reaction products are carried out by known processes.

The active compounds according to the invention have a potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris pv. oryzae;*

Pseudomonas species, such as, for example, *Pseudomonas syringae pv. lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae,*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Sclerotinia species, such as, for example, *Sclerotinia sclerotiorum;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;* and

Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling diseases in viticulture and fruit and vegetable growing, such as, for example, against Phytophtora and Plasmopara species. The compounds according to the invention can also be employed for increasing the harvest of crop plants.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to use for example organic solvents as auxiliary solvents. Essentially, the following are suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides aldimorph, ampropylfos, ampropylfos potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticdiin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos(IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene(PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole,
validamycin A, vinclozolin, viniconazole,
zarilamide, zineb, ziram and also
Dagger G,
OK-8705,
OK-8801, α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
1-isopropyl {2-methyl-1-[[[1-(4-methylpheny)ethyl]amino]carbonyl]propyl}-carbamate,
1-(2,4-dichlorophenyl)-2-(1H-1,2,4-triazol-1-yl)ethanone-O-(phenylmethyl)-oxime,
1-(2-methyl-1-naphthalenyl)-1H-pyrrol-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)methoxy]phenyl]ethenyl]-1H-imidazole,
1-methyl-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,2-dichloro-N-[1-(4-chlorophenyl)ethyl]-1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)phenyl]methyl]-benzamide,
2-(2,3,3-triiodo-2-propenyl)-2H-tetrazole,
2-[(1-methylethyl)sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol(OPP),
3,4-dichloro-1-[4-(difluoromethoxy)-phenyl]-1H-pyrrol-2,5-dione,
3,5-dichloro-N-[cyano[(1-methyl-2-propynyl)oxy]methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methaneamine,
8-hydroxyquinolinesulphate,
9H-xanthene-2-[(phenylamino)-carbonyl]-9-carboxylihydrazide,
bis-(1-methylethyl)-3-methyl-4-[(3-methylbenzoyl)oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride,
ethyl[(4-chlorophenyl)-azo]-cyanoacetate,
potassium bicarbonate,
methanetetrathiol, -sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methaneimideamide,
N-formyl-N-hydroxy-DL-alanine,-sodium salt,
O,O-diethyl[2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one, Bactericides
bromopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.
Insecticides/Acaricides/Nematicides
abamectin, acephate, acrinathrin, alanycarb, aldicarb, alphamethrin, amitraz, avermectin, AZ 60541, azadirachtin, azinphos A, azinphos M; azocyclotin,
*Bacillus thuringiensis,* 4-bromo-2-(4-chlorophenyl)-1-(ethoxymethyl)-5-(tri-fluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxin, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethaneimideamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine,
deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton,
edifenphos, emamectin, esfenvalerate, ethiofencarb, ethion, ethofenprox, ethoprophos, etrimphos,
fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, firathiocarb,
HCH, heptenophos, hexaflumuron, hexythiazox,
imidacloprid, iprobenfos, isazophos, isofenphos, isoprocarb, isoxathion, ivermectin,
lambda-cyhalothrin, lufenuron,
malathion, mecarbam, mervinphos, mesulfenphos, metaldehyde, methacrifos, methamidophos, methidathion, methiocarb, methomyl, metolcarb, milbemectin, monocrotophos, moxidectin,
naled, NC 184, nitenpyram,
omethoate, oxamyl, oxydemethon M, oxydeprofos,
parathion A, parathion M, permethrin, phenthoate, phorate, phosalone, phosmet, phosphamidon, phoxim, pirimicarb, pirimiphos M, pirimiphos A, profenophos, promecarb, propaphos, propoxur, prothiophos, prothoate, pymetrozin, pyrachlophos, pyridaphenthion, pyresmethrin, pyrethrum, pyridaben, pyrimidifen, pyriproxifen,
quinalphos,
salithion, sebufos, silafluofen, sulfotep, sulprofos,
tebufenozide, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb,
vamidothion, XMC, xylylcarb, zetamethrin.

It is also possible to admix other known active compounds, such as herbicides, fertilizers and growth regulators.

The active compounds can be used as such or in the form of their commercial formulations or the use forms prepared therefrom, such as ready-to-use solutions, suspensions, wettable powders, pastes, soluble powders, dusts and granules. They are used in the customary manner, for example by pouring, spraying, atomizing, broadcasting, foaming, brushing-on and the like. It is further possible to apply the active compounds by the ultra-low volume method or to inject the preparation of active compound, or the active compound itself, into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of from 0.001 to 50 g, preferably 0.01 to 10 g, are generally required per kilogram of seed.

In the treatment of the soil, active compound concentrations of from 0.00001 to 0.1% by weight, preferably from 0.0001 to 0.02% by weight, are required at the site of action.

PREPARATION EXAMPLES

Example 1

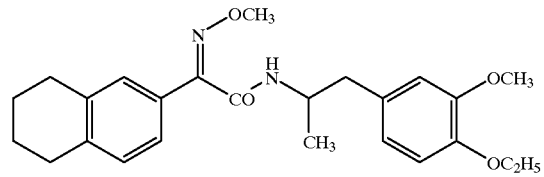

Process a)

At −20° C., a solution of 0.5 g (3.8 mmol) of isobutyl chloroformate in 5 ml of dichloromethane is added dropwise over a period of 10 minutes to a solution of 0.886 g (3.8 mmol) of 2-hydroximino-2-(2-tetrahydronaphthyl)acetic acid in 10 ml of dichloromethane, the mixture is stirred for 10 minutes, 0.53 g (3.8 mmol) of triethylamine are added and the mixture is stirred without further cooling for another hour, during which the solution warms to −5° C. The reaction mixture is then once more cooled to −20° C., a solution of 0.81 g (3.8 mmol) of 2-(4-ethoxy-3-methoxyphenyl)-1-methylethylamine in 15 ml of dichloromethane is added dropwise and the mixture is stirred without further cooling for another 15 hours. The reaction mixture is washed successively with water, 0.1 N hydrochloric acid and again with water, dried over sodium sulphate and concentrated under reduced pressure. The residue is chromatographed over silica gel using petroleum ether/ethyl acetate (2:1). This gives two fractions, the second of which contains the product. The second fraction is once more chromatographed over silica gel in an MPLC apparatus using cyclohexane/ethyl acetate.

This gives 0.1 g (6% of theory) of N-[2-(4-ethoxy-3-methoxyphenyl)-1-methylethyl]-2-methoxyimino-2-(5,6,7,8-tetrahydronaphthalin-2-yl)-acetic acid amide.

HPLC: logP: 3.72/4.04

Similarly to Example 1, and in accordance with the general description of the preparation process according to the invention, it is also possible to prepare the compounds of the formula (I-m) listed in Table 7 below:

TABLE 7
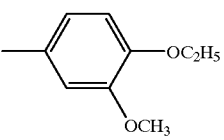
| Ex. No. | R¹ | R² | R⁴ | isomer | logP |
|---|---|---|---|---|---|
| 2 | 4-bromophenyl | —O—CH₃ | 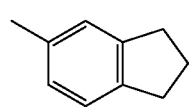 | E/Z | 3.34/3.64 |
| 3 | 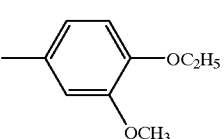 | —O—CH₃ | 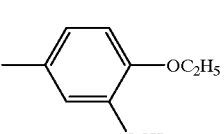 | E/Z | 3.13/3.44 |
| 4 | 4-chlorophenyl | —O—CH₃ | 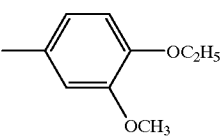 | E/Z | 3.26/3.56 |
| 5 | 4-bromophenyl | —O—CH₃ | 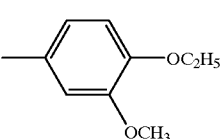 | Z | 3.64 |
| 6 | 4-bromophenyl | —O—CH₃ | 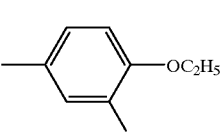 | E | 3.34 |
| 7 | 4-chlorophenyl | —O—CH₃ | 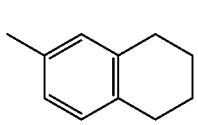 | E | 3.26 |
| 8 | 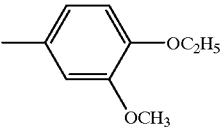 | —O—C₂H₅ | 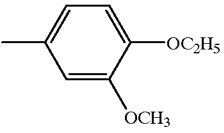 | E/Z | 4.07/4.41 |
| 9 | 4-bromophenyl | —O—C₂H₅ | | E/Z | 3.69/4.01 |

TABLE 7-continued

[Structure: R¹-C(=O)-C(=N-R²)-NH-CH(CH₃)-CH₂-R⁴, with wavy bond on R²-N]

| Ex. No. | R¹ | R² | R⁴ | isomer | logP |
|---|---|---|---|---|---|
| 10 | 4-tolyl | —O—CH₃ | 4-methyl-2-methoxy-3-ethoxyphenyl (3-OC₂H₅, 2-OCH₃) | E/Z | 3.04/3.34 |
| 11 | 4-chlorophenyl | —O—C₂H₅ | 4-methyl-2-methoxy-3-ethoxyphenyl | E/Z | 3.59/3.91 |
| 12 | 6-methyl-1,2,3,4-tetrahydronaphthyl | —O—C₂H₅ | 4-methyl-2-methoxy-3-ethoxyphenyl | OC2H5 | 4.41 |
| 13 | 6-methyl-1,2,3,4-tetrahydronaphthyl | —O—C₂H₅ | 4-methyl-2-methoxy-3-ethoxyphenyl | E | 4.07 |
| 14 | 4-tolyl | —O—C₂H₅ | 4-methyl-2-methoxy-3-ethoxyphenyl | E/Z | 3.38/3.71 |
| 15 | 4-ethylphenyl | —O—C₂H₅ | 4-methyl-2-methoxy-3-ethoxyphenyl | E/Z | 3.73/4.05 |
| 16 | 5-methyl-2,3-dihydro-1H-indenyl | —O—C₂H₅ | 4-methyl-2-methoxy-3-ethoxyphenyl | E/Z | 3.79/4.10 |
| 17 | 5-methyl-2,3-dihydro-1H-indenyl | —O—C₂H₅ | 4-methyl-2-methoxy-3-ethoxyphenyl | Z | 4.10 |

TABLE 7-continued

![structure: R1-C(=NR2)-C(=O)-NH-CH(CH3)-R4]

| Ex. No. | R¹ | R² | R⁴ | isomer | logP |
|---|---|---|---|---|---|
| 18 | (5-methylindan-yl) | —O—C₂H₅ | phenyl with 4-OC₂H₅, 3-OCH₃ | E | 3.79 |
| 19 | 4-ethylphenyl | —O—C₂H₅ | phenyl with 4-OC₂H₅, 3-OCH₃ | Z | 4.05 |
| 20 | 4-bromophenyl | —O—C₂H₅ | phenyl with 4-OC₂H₅, 3-OCH₃ | E | 3.69 |

Example A
Phytophthora Test (Tomato)/protective

Solvent: 47 parts by weight of acetone

Emulsifier: 3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of Phytophthora infestans. The plants are then placed in an incubation cabin at approximately 20° C. and 100% relative atmospheric humidity.

Evaluation is carried out 3 days after the inoculation. 0% means an efficacy which corresponds to that of the control, while an efficacy of 100% means that no infection is observed. In this test, the compounds according to the invention listed in Examples (1), (6), (7), (11), (13) and (14) exhibit, at an application rate of 50 g/ha, an efficacy of 86% or more.

Example B
Plasmopara Test (Grapevine)/protective

Solvent: 47 parts by weight of acetone

Emulsifier: 3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of Plasmopara viticola and then remain in an incubation cabin at approximately 20° C. and 100% relative atmospheric humidity for 1 day. The plants are subsequently placed in a greenhouse at approximately 21° C. and approximately 90% relative atmospheric humidity for 5 days. The plants are then moistened and placed in an incubation cabin for 1 day.

Evaluation is carried out 6 days after the inoculation. 0% means an efficacy which corresponds to that of the control, while an efficacy of 100% means that no infection is observed.

In this test, the substances according to the invention listed in Examples (6), (7) and (14) exhibit, at an application rate of 50 g/ha, an efficacy of 96% or more.

What is claimed is:

1. A compound of the formula (I)

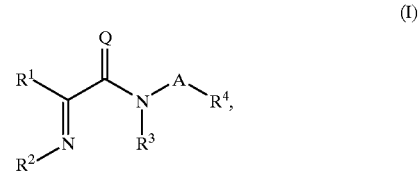

in which

A represents —CH(CH₃)—CH₂—, or represents a grouping —O—*CH₂—, —NH—*CH₂—, —N(CH₃)—*CH₂—, where the atom labelled with * is attached to R⁴, or represents cyclopropane-1,2-diyl, cyclobutane-1,2-diyl, cyclopentane-1,2-diyl, cyclohexane-1,2-diyl, cycloheptane-1,2-diyl or o-phenylene, each of which is optionally mono- to trisubstituted by identical or different substituents selected from the group consisting of methyl, ethyl, fluorine, chlorine, cyano and methoxy, Q represents oxygen or sulphur, $R^1$ represents in each case optionally mono- to trisubstituted cyclobutyl, cyclopentyl, cyclohexyl, phenyl, or naphthyl, where the substituents are selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoro-ethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, cyclopropyl, cyclobutyl, cyclopentyl or cyclohexyl, or $R^1$ represents phenyl or naphthyl having a fused-on cyclopropyl, cyclobutyl, cyclopentyl, cyclohexyl, cycloheptyl cyclooctyl or cyclononyl ring, where the cycloalkyl moiety is optionally mono- to tetrasubstituted by methyl, ethyl, n- or i-propyl, n-, i-, s- or t-butyl and where the phenyl or naphthyl ring optionally carries the substituents mentioned for $Y^1$ to $Y^8$, or represents a tricycle

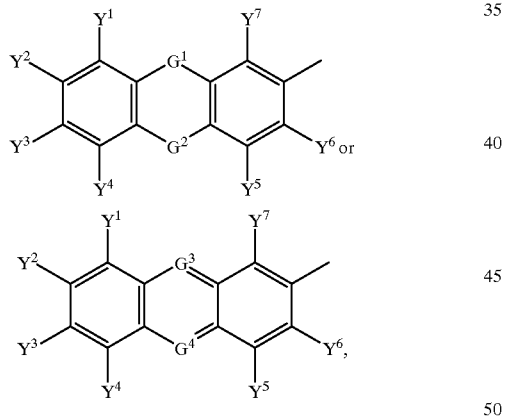

in which $G^1$ and $G^2$ independently of one another in each case represent a single bond, ethanediyl, ethanediyl, propanediyl, ethenediyl, or carbonyl and $G^3$ and $G^4$ independently of one another each represent a grouping

and $Y^1, Y^2, Y^3, Y^4, Y^5, Y^6, Y^7$ and $Y^8$ independently of one another each represent hydrogen, fluorine, chlorine, bromine, cyano, nitro, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methyl-sulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, cyclopropyl, cyclobutyl, cyclopentyl or cyclohexyl, $R^2$ represents hydroxyl, amino or in each case optionally fluorine-, chlorine-, cyano-, methoxy- or ethoxy-substituted methyl, ethyl, n- or i-propyl, n-, i-, s- or t-butyl, vinyl, allyl, propargyl, methoxy, ethoxy, allyloxy, propargyloxy, methylamino, ethylamino, dimethylamino, in each case optionally fluorine-, chlorine-, cyano-, methyl-, ethyl-, methoxy- or ethoxy-substituted cyclopropyl, cyclobutyl, cyclopentyl, cyclohexyl, cyclopentyloxy, cyclohexyloxy, cyclopentylamino, cyclohexylamino or in each case optionally substituted phenyl, benzyl, benzyloxy, naphthyl, or phenylamino, where the substituents are selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methyl-sulphonyloxy, ethylsulphonyloxy, hydroximinomethyl, hydroximinoethyl, methoximinomethyl, ethoximinomethyl, methoximinoethyl or ethoximinoethyl, in each case doubly attached trimethylene (propane-1,3-diyl), tetramethylene (butane-1,4-diyl), methylenedioxy or ethylenedioxy, each of which is optionally mono- or polysubstituted by identical or different substituents selected from the group consisting of fluorine, chlorine, methyl, trifluoromethyl, ethyl, n- or i-propyl, cyclopropyl, cyclobutyl, cyclopentyl or cyclohexyl, or $R^2$ represents one of the groupings below:

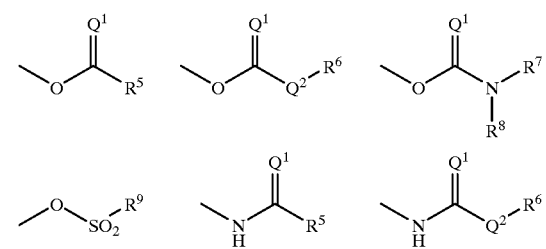

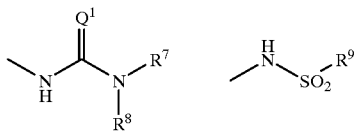

in which

Q¹ and Q² independently of one another each represent oxygen or sulphur,

R⁵ represents hydrogen or methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, R⁶ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, R⁷ represents hydrogen, methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, R⁸ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, R⁹ represents methyl, ethyl, n- or i-propyl, n-, i-, s- or t-butyl, dimethylamino, diethylamino, or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, R³ represents hydrogen or represents methyl or ethyl, R⁴ represents in each case optionally mono- to trisubstituted cyclopropyl, cyclobutyl, cyclopentyl or cyclohexyl, phenyl, or naphthyl, where the substituents are selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluoro-chloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methyl-sulphonyloxy, ethylsulphonyloxy, hydroximinomethyl, hydroximinoethyl, methoximinomethyl, ethoximinomethyl, methoximinoethyl or ethoximinoethyl, in each case doubly attached trimethylene (propane-1,3-diyl), tetramethylene (butane-1,4-diyl), methylenedioxy or ethylenedioxy, each of which is optionally mono- or polysubstituted by identical or different substituents selected from the group consisting of fluorine, chlorine, methyl, trifluoromethyl, ethyl, n- and i-propyl, cyclopropyl, cyclobutyl, cyclopentyl or cyclohexyl.

2. A compound of the formula (I) according to claim 1 in which

A represents —CH(CH₃)—CH₂—, or represents a grouping —O—*CH₂—, —NH—*CH₂—, —N(CH₃)—*CH₂—, where the atom labelled with * is attached to R⁴, or represents cyclopropane-1,2-diyl, cyclobutane-1,2-diyl, cyclopentane-1,2-diyl, cyclohexane-1,2-diyl, cycloheptane-1,2-diyl or o-phenylene, each of which is optionally mono- to trisubstituted by identical or different substituents selected from the group consisting of methyl, ethyl, fluorine, chlorine, cyano and methoxy, Q represents oxygen or sulphur, R¹ represents in each case optionally mono- to trisubstituted cyclobutyl, cyclopentyl, cyclohexyl, phenyl, or naphthyl, where the substituents are selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl, ethoximinoethyl, cyclopropyl, cyclobutyl, cyclopentyl or cyclohexyl, or R¹ represents a grouping

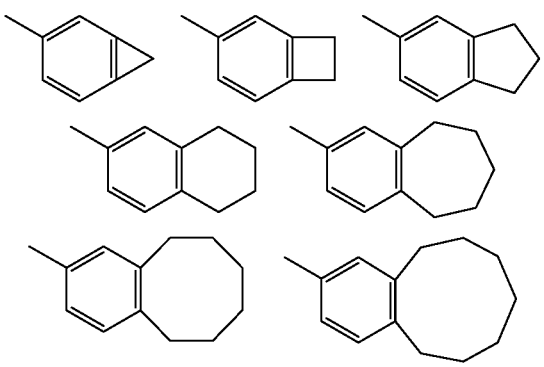

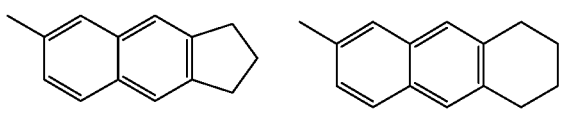
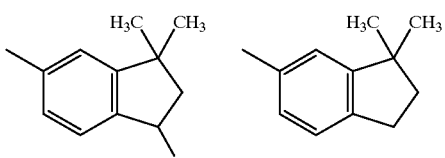
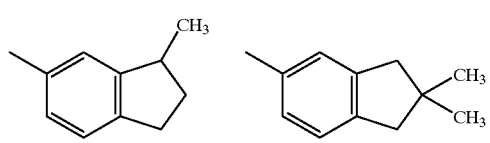

which optionally carries the substituents mentioned for $Y^1$ to $Y^8$ on the phenyl or naphthyl moiety, or $R^1$ represents a tricycle

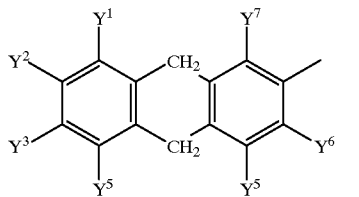
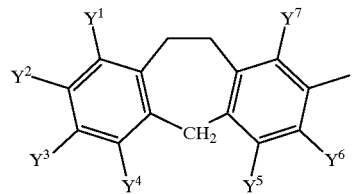
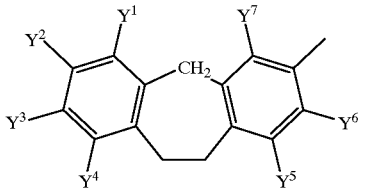
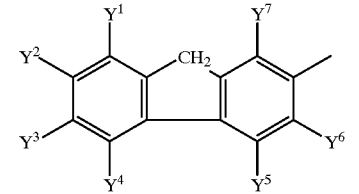
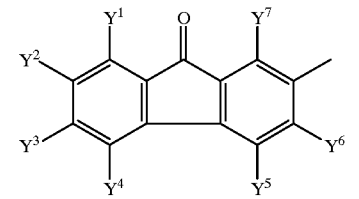

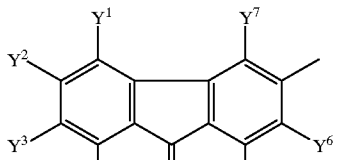
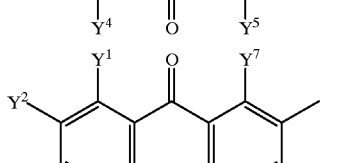
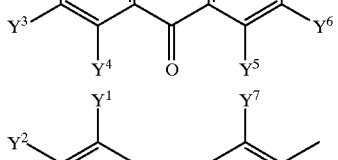
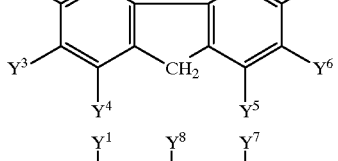
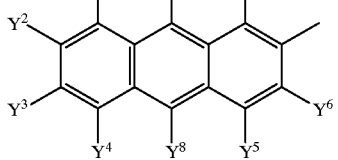
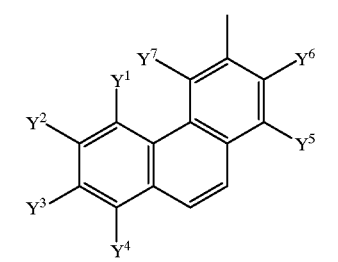

in which $Y^1, Y^2, Y^3, Y^4, Y^5, Y^6, Y^7$ and $Y^8$ independently of one another each represent hydrogen, fluorine, chlorine, bromine, cyano, nitro, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, cyclopropyl, cyclobutyl, cyclopentyl or cyclohexyl, $R^2$ represents hydroxyl, amino, methyl, fluoromethyl, difluoromethyl, trifluoromethyl, cyanophenyl, ethyl, n- or i-propyl, n-, i-, s- or t-butyl, vinyl, allyl, methoxy, fluoromethoxy, difluoromethoxy, difluorochloromethoxy, trifluoromethoxy, cyanomethoxy, ethoxy, allyloxy, methylamino, ethylamino, dimethylamino, cyclopropyl, cyclobutyl, cyclopentyl, cyclohexyl, cyclopentyloxy, cyclohexyloxy, cyclopentylamino, cyclohexylamino or in each case optionally substituted phenyl, benzyl, benzyloxy, naphthyl, or phenylamino, where the substituents are selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methyl-sulphonyloxy, ethylsulphonyloxy, hydroximinomethyl, hydroximinoethyl, methoximinomethyl, ethoximinomethyl, methoximinoethyl or ethoximinoethyl, in each case doubly attached trimethylene (propane-1,3-diyl), tetramethylene (butane-1,4-diyl), methylenedioxy or ethylenedioxy, each of which is optionally mono- or polysubstituted by identical or different substituents selected from the group consisting of fluorine, chlorine, methyl, trifluoromethyl, ethyl, n- or i-propyl; cyclopropyl, cyclobutyl, cyclopentyl or cyclohexyl, or R² represents one of the groupings below:

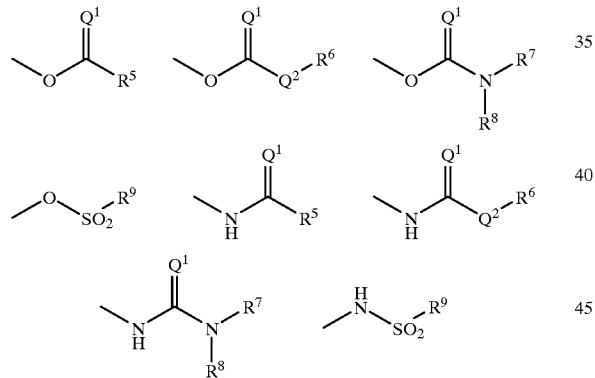

in which

Q¹ and Q² independently of one another each represent oxygen or sulphur,

R⁵ represents hydrogen or methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, R⁶ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, R⁷ represents hydrogen, methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, R⁸ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, R⁹ represents methyl, ethyl, n- or i-propyl, n-, i-, s- or t-butyl, dimethylamino, diethylamino, or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, R³ represents hydrogen or represents methyl or ethyl, R⁴ represents in each case optionally mono- to trisubstituted cyclopropyl, cyclobutyl, cyclopentyl or cyclohexyl, phenyl, or naphthyl, where the substituents are selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethyl-sulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methyl-sulphonyloxy, ethylsulphonyloxy, hydroximinomethyl, hydroximinoethyl, methoximinomethyl, ethoximinoethyl, methoximinoethyl or ethoximinoethyl, in each case doubly attached trimethylene (propane-1,3-diyl), tetramethylene (butane-1,4-diyl), methylenedioxy or ethylenedioxy, each of which is optionally mono- or polysubstituted by identical or different substituents selected from the group consisting of fluorine, chlorine, methyl, trifluoromethyl, ethyl, n- and i-propyl, cyclopropyl, cyclobutyl, cyclopentyl or cyclohexyl.

3. A compound of the formula

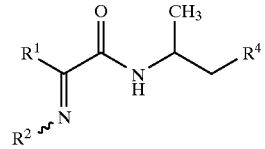

wherein

R¹ represents 4-chlorophenyl,

R² represents —O—CH₃, and

R⁴ represents

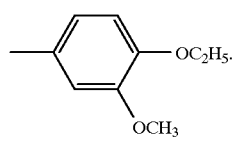

4. A pesticide composition comprising at least one compound of the formula (I) according to claim 1 and one or more extenders and/or surfactants.

5. A method for controlling pests, comprising the step of applying a pesticidally effective amount of a compound of the formula (I) according to claim 1 to pests and/or their habitat or to an area from which it is desired to exclude pests.

6. A process for preparing a pesticide, comprising the step of mixing a compound of the formula (I) according to claim 1 with extenders and/or surfactants.

7. A process for preparing a compound of the formula (I)

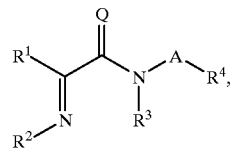

(I)

according to claim 3, in which

Q represents oxygen or sulphur, $R^1$ represents in each case optionally substituted cycloalkyl, cycloalkenyl, or aryl, $R^1$ represents aryl having a fused-on cycloalkyl ring where both the aryl moiety and the cycloalkyl moiety optionally carry further substituents, or $R^1$ represents a tricycle

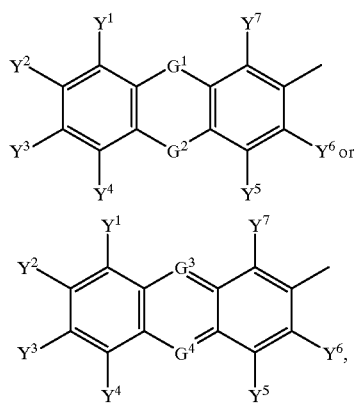

in which $G^1$ and $G^2$ independently of one another each represent a single bond, alkanediyl, alkenediyl, or carbonyl, $G^3$ and $G^4$ independently of one another each represent a grouping

and $Y^1, Y^2, Y^3, Y^4, Y^5, Y^6, Y^7$ and $Y^8$ independently of one another each represent hydrogen, halogen, cyano, nitro, in each case optionally substituted alkyl, alkoxy, alkylamino, dialkylamino, alkylthio, alkylsulphinyl, alkylsulphonyl or cycloalkyl, $R^2$ represents hydroxyl, amino or in each case optionally substituted alkyl, alkenyl, alkinyl, alkoxy, alkenyloxy, alkinyloxy, alkylamino, dialkylamino, arylamino, cycloalkyl, cycloalkenyl, cycloalkoxy, cycloalkenyloxy, cycloalkylamino, aryl, arylalkyl, arylalkoxy or one of the following groupings:

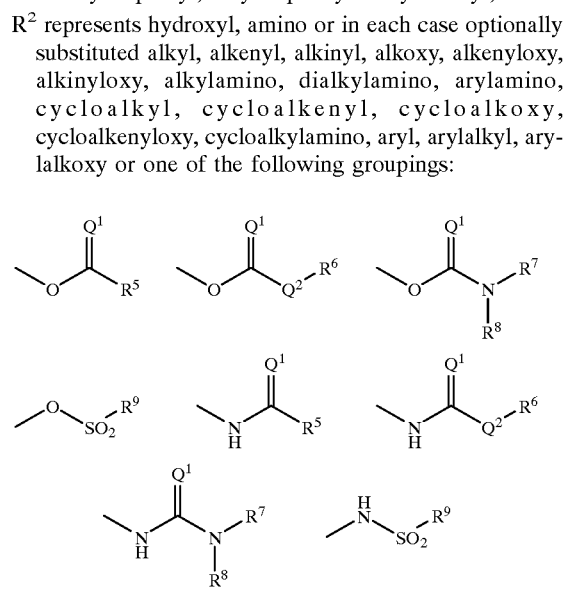

in which $Q^1$ and $Q^2$ independently of one another each represent oxygen or sulphur, $R^5$ represents hydrogen or optionally substituted alkyl or aryl, $R^6$ represents optionally substituted alkyl or aryl, $R^7$ represents hydrogen or optionally substituted alkyl or aryl, $R^8$ represents optionally substituted alkyl or aryl, or $R^9$ represents optionally substituted alkyl, dialkylamino, or represents aryl, $R^3$ represents hydrogen or in each case optionally substituted alkyl, alkenyl, alkinyl or cycloalkyl, $R^4$ represents in each case optionally substituted cycloalkyl, cycloalkenyl, or aryl, comprising reacting
a) a carboxylic acid derivative of the general formula (II)

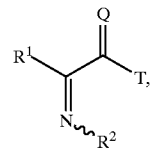

(II)

in which $R^1$, $R^2$ and Q are each defined as in claim 3 and

T represents hydroxyl, halogen or alkoxy, with an amine of the general formula (III)

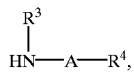
(III)

in which

R³, R⁴ and A are each defined as in claim 3
—or with a hydrogen halide thereof—optionally in the presence of an acid acceptor, optionally in the presence of a condensing agent and optionally in the presence of a diluent, or b) a glyoxylic acid amide of the general formula (IV)

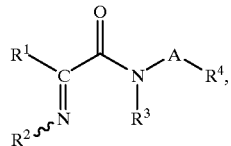
(IV)

in which

A, R¹, R², R³ and R⁴ are each defined as in claim 3, with a sulphurizing agent, optionally in the presence of a diluent, or c) a glyoxylic acid derivatives of the formula (V)

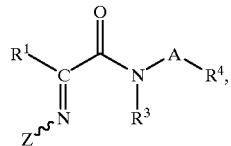
(V)

in which

A, Q, R¹, R³ and R⁴ are each defined as in claim 3 and

Z represents hydroxyl or amino, with an activated acid derivative of one of the formulae (VI) to (XIII),

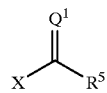
(VI)

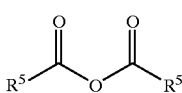
(VII)

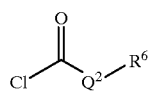
(VIII)

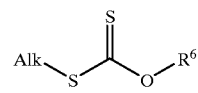
(IX)

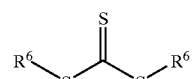
(X)

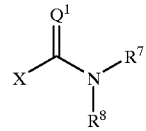
(XI)

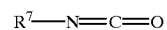
(XII)

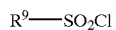
(XIII)

in which

R⁵, R⁶, R⁷, R⁸ and R⁹ are each defined as in claim 3, optionally in the presence of a diluent and optionally in the presence of a base.

8. A compound of the formula (IV)

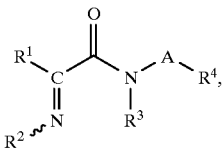
(IV)

in which

A, R¹, R², R³ and R⁴ are each as defined in claim 7.

9. A compound of the formula (V)

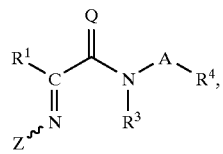
(V)

in which

A, Q, R¹, R³ and R⁴ are each as defined claim 7 and

Z represent hydroxyl or amino.

* * * * *

UNITED STATES PATENT AND TRADEMARK OFFICE
CERTIFICATE OF CORRECTION

PATENT NO. : 6,313,173 B1
DATED : November 6, 2001
INVENTOR(S) : Thomas Seitz et al.

It is certified that error appears in the above-identified patent and that said Letters Patent is hereby corrected as shown below:

Column 57,
Line 30, change:   which optionally carries the substituents mentioned for
$Y^1$ to $Y^8$ on the phenyl or naphthyl moiety, or
$R^1$ represents a tricycle

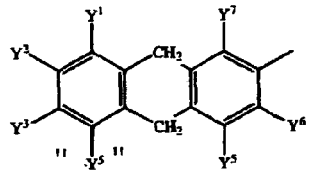

to:   which optionally carries the substituents mentioned for
$Y^1$ to $Y^8$ on the phenyl or naphthyl moiety, or
$R^1$ represents a tricycle

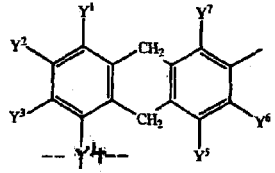

Signed and Sealed this

Sixteenth Day of September, 2003

JAMES E. ROGAN
*Director of the United States Patent and Trademark Office*